United States Patent
Teoh et al.

(10) Patent No.: US 12,256,939 B2
(45) Date of Patent: Mar. 25, 2025

(54) VASO-OCCLUSIVE DEVICE DELIVERY SYSTEM

(71) Applicants: STRYKER CORPORATION, Kalamazoo, MI (US); STRYKER EUROPEAN OPERATIONS HOLDINGS LLC, Kalamazoo, MI (US)

(72) Inventors: Clifford Teoh, Los Altos, CA (US); Timothy Odell, Fremont, CA (US); Hancun Chen, San Ramon, CA (US); Lantao Guo, San Ramon, CA (US); Richard Murphy, Sunnyvale, CA (US)

(73) Assignees: Stryker Corporation, Kalamazoo, MI (US); Stryker European Operations Holdings, LLC, Kalamazoo, MI (US)

( * ) Notice: Subject to any disclaimer, the term of this patent is extended or adjusted under 35 U.S.C. 154(b) by 0 days.

(21) Appl. No.: 18/189,169

(22) Filed: Mar. 23, 2023

(65) Prior Publication Data

US 2023/0225738 A1    Jul. 20, 2023

Related U.S. Application Data

(63) Continuation of application No. 16/711,327, filed on Dec. 11, 2019, now Pat. No. 11,622,772, which is a continuation of application No. 15/664,247, filed on Jul. 31, 2017, now Pat. No. 10,537,333, which is a
(Continued)

(51) Int. Cl.
*A61B 17/12*    (2006.01)

(52) U.S. Cl.
CPC .... *A61B 17/1214* (2013.01); *A61B 17/12031* (2013.01); *A61B 2017/12068* (2013.01);
(Continued)

(58) Field of Classification Search
CPC .......... A61B 17/1214; A61B 17/12031; A61B 17/12154; A61B 2017/12068; A61B 2017/12077; A61B 2017/1209
See application file for complete search history.

(56) References Cited

U.S. PATENT DOCUMENTS

| | | | | |
|---|---|---|---|---|
| 4,512,338 | A * | 4/1985 | Balko | A61F 2/966 606/151 |
| 2010/0004731 | A1* | 1/2010 | Gandhi | A61B 17/12 623/1.11 |
| 2010/0063572 | A1* | 3/2010 | Teoh | A61B 17/0057 606/191 |

OTHER PUBLICATIONS

Notification of the Second Office Action and related Search Report for Chinese Application No. 2014800128713, dated Sep. 18, 2017, in Chinese language with translation provided by Chinese associate (11 pages).
(Continued)

*Primary Examiner* — Richard G Louis
(74) *Attorney, Agent, or Firm* — Vista IP Law Group, LLP

(57) ABSTRACT

A vaso-occlusive device delivery assembly includes a pusher assembly having proximal and distal ends, a conductive sacrificial link disposed at the distal end of the pusher assembly, and a vaso-occlusive device secured to the pusher assembly by the sacrificial link. The pusher assembly includes first and second conductors extending between the proximal and distal ends thereof. The sacrificial link is electrically coupled between the first and second conductors, such that the first conductor, sacrificial link and second conductor form an electrical circuit, and, when a disintegration current is applied through the sacrificial link through the first and second conductors, the sacrificial link thermally disintegrates, thereby releasing the attachment member and vaso-occlusive device from the pusher assembly.

13 Claims, 24 Drawing Sheets

Related U.S. Application Data continuation of application No. 14/206,176, filed on Mar. 12, 2014, now Pat. No. 9,717,502.

(60) Provisional application No. 61/785,730, filed on Mar. 14, 2013.

(52) U.S. Cl.
CPC .............. *A61B 2017/12077* (2013.01); *A61B 2017/1209* (2013.01); *A61B 17/12154* (2013.01)

(56) References Cited

OTHER PUBLICATIONS

Notice of Rejection for Japanese Patent Application No. 2018-122605 dated Jul. 23, 2019, in Japanese only.
English language listing of the pending claims for JP Appl. No. 2018-122605 as of Jul. 24, 2019.
Extended European Search Report for EP Patent Application No. EP 15189893.9, dated Mar. 18, 2016 (5 pages).
PCT Notification of Transmittal of the International Search Report and the Written Opinion of the International Searching Authority for PCT/US2014/024291, mailed Aug. 7, 2014, Stryker Corporation., International filing date Mar. 12, 2014. PCT/ISA/220 (6 pages).
PCT International Search Report and Written Opinion for International Application No. PCT/US2014/024291, Applicant Stryker Corporation, forms PCT/ISA/210, 220, and 237, dated Nov. 24, 2014 (15 pages).

\* cited by examiner

VASO-OCCLUSIVE DEVICE DELIVERY SYSTEM

RELATED APPLICATION DATA

The present application is a continuation of U.S. patent application Ser. No. 16/711,327, filed Dec. 11, 2019, now U.S. Pat. No. 11,622,772, which is a continuation of U.S. patent application Ser. No. 15/664,247, filed Jul. 31, 2017, now U.S. Pat. No. 10,537,333, which is a continuation of U.S. patent application Ser. No. 14/206,176, filed Mar. 12, 2014, now U.S. Pat. No. 9,717,502, which claims the benefit under 35 U.S.C. § 119 to U.S. Provisional Application Ser. No. 61/785,730, filed Mar. 14, 2013. The foregoing applications are hereby incorporated by reference into the present application in their entirety.

FIELD

The field of the disclosed inventions generally relates to systems and delivery devices for implanting vaso-occlusive devices for establishing an embolus or vascular occlusion in a vessel of a human or veterinary patient. More particularly, the disclosed inventions relate to detachment using a thermally disintegrable link.

BACKGROUND

Vaso-occlusive devices or implants are used for a wide variety of reasons, including treatment of intra-vascular aneurysms. Commonly used vaso-occlusive devices include soft, helically wound coils formed by winding a platinum (or platinum alloy) wire strand about a "primary" mandrel. The coil is then wrapped around a larger, "secondary" mandrel, and heat treated to impart a secondary shape. For example, U.S. Pat. No. 4,994,069, issued to Ritchart et al., which is fully incorporated herein by reference as though set forth in full, describes a vaso-occlusive device that assumes a linear, helical primary shape when stretched for placement through the lumen of a delivery catheter, and a folded, convoluted secondary shape when released from the delivery catheter and deposited in the vasculature.

In order to deliver the vaso-occlusive devices to a desired site in the vasculature, e.g., within an aneurysmal sac, it is well-known to first position a small profile, delivery catheter or "micro-catheter" at the site using a steerable guidewire. Typically, the distal end of the micro-catheter is provided, either by the attending physician or by the manufacturer, with a selected pre-shaped bend, e.g., 45°, 26°, "J", "S", or other bending shape, depending on the particular anatomy of the patient, so that it will stay in a desired position for releasing one or more vaso-occlusive device(s) into the aneurysm once the guidewire is withdrawn. A delivery or "pusher" wire is then passed through the micro-catheter, until a vaso-occlusive device coupled to a distal end of the pusher assembly is extended out of the distal end opening of the micro-catheter and into the aneurysm. Once in the aneurysm, segments of some vaso-occlusive devices break off to allow more efficient and complete packing. The vaso-occlusive device is then released or "detached" from the end of the pusher assembly, and the pusher assembly is withdrawn back through the catheter. Depending on the particular needs of the patient, one or more additional occlusive devices may be pushed through the catheter and released at the same site.

One well-known way to release a vaso-occlusive device from the end of the pusher assembly is through the use of an electrolytically severable junction, which is a small exposed section or detachment zone located along a distal end portion of the pusher assembly. The detachment zone is typically made of stainless steel and is located just proximal of the vaso-occlusive device. An electrolytically severable junction is susceptible to electrolysis and electrolytically disintegrates when the pusher assembly is electrically charged in the presence of an ionic solution, such as blood or other bodily fluids. Thus, once the detachment zone exits out of the catheter distal end and is exposed in the vessel blood pool of the patient, a current applied through an electrical contact to the conductive pusher completes an electrolytic detachment circuit with a return electrode, and the detachment zone disintegrates due to electrolysis.

While electrolytically severable junctions have performed well, there remains a need for other systems and methods for delivering vaso-occlusive devices into vessel lumens.

SUMMARY

In one embodiment of the disclosed inventions, a vaso-occlusive device delivery assembly includes a pusher assembly having proximal and distal ends, a conductive sacrificial link disposed at the distal end of the pusher assembly, and a vaso-occlusive device secured to the pusher assembly by the sacrificial link. The pusher assembly includes first and second conductors extending between the proximal and distal ends thereof. The sacrificial link is electrically coupled between the first and second conductors, such that the first conductor, sacrificial link and second conductor form an electrical circuit, and, when a disintegration current is applied through the sacrificial link through the first and second conductors, the sacrificial link thermally disintegrates, thereby releasing the attachment member and vaso-occlusive device from the pusher assembly.

In some embodiments, the vaso-occlusive device delivery assembly also includes an attachment member secured to the vaso-occlusive device and secured to the pusher assembly by the sacrificial link. The attachment member may include a meltable tether, such that, when a heating current, less than the disintegration current, is applied through the sacrificial link through the first and second conductors, the sacrificial link is heated by resistive heating to a temperature sufficient to sever the meltable tether without disintegrating the sacrificial link, thereby detaching the vaso-occlusive device from the pusher assembly.

In some embodiments, the vaso-occlusive device delivery assembly includes a power supply electrically connected to the first and second conductors, where the power supply is controllable to selectively deliver the disintegration current or the heating current through the sacrificial link. The vaso-occlusive device delivery assembly may also include a third conductor extending between the proximal and distal ends of the pusher assembly and electrically connected to the sacrificial link, such that the third conductor, sacrificial link, and second conductor form an electrical circuit, where the third conductor has a greater resistivity than the first conductor, such that, when the disintegration current is applied through the sacrificial link through the third and second conductors, the sacrificial link is heated by resistive heating to a temperature sufficient to melt the tether without disintegrating the sacrificial link.

In some embodiments, the pusher assembly also includes first and second load bearing connectors that electrically and mechanically connect the sacrificial link to the respective first and second conductors. The sacrificial link and the load bearing conductor may be mechanically tied to each other.

The pusher assembly may also include a cylindrical body disposed around and thermally insulating the sacrificial link, where the cylindrical body defines a cavity in which the sacrificial link is located.

In some embodiments, the sacrificial link includes an electrically conductive polymer tube defining an axial lumen, where a distal end of the first conductor is disposed within the axial lumen. The electrically conductive polymer tube may have a radially enlarged distal portion, and a proximal end of the vaso-occlusive device may be secured to the polymer tube by an interference fit with the radially enlarged distal portion. In other embodiments, the proximal end of the vaso-occlusive device may be secured to the polymer tube by an adhesive, a weld, or mechanical bonding.

In other embodiments, the sacrificial link includes an elongate link member defining a longitudinal bore therein and a proximal end opening in communication with the longitudinal bore, where the bore has a closed distal end, and where a distal end of the first conductor extends into the longitudinal bore. In some of those embodiments, the distal end of the first conductor includes a protrusion extending obliquely to a longitudinal axis of the first conductor and configured to strengthen a mechanical connection between the first conductor and the sacrificial link. In some others of those embodiments, the distal end of the first conductor includes a radially enlarged portion configured to concentrate current density and to strengthen a mechanical connection between the first conductor and the sacrificial link.

In some embodiments, the pusher assembly defines a lumen, and the first and second conductors extend between the proximal and distal ends of the pusher assembly in the lumen. In other embodiments, the second conductor is a conductive tubular pusher conduit extending between the proximal and distal ends of the pusher assembly, and the first conductor extends between the proximal and distal ends of the pusher assembly through the pusher conduit.

In another embodiment of the disclosed inventions, a vaso-occlusive device is attached to a pusher assembly secured thereto by a connection formed between a sacrificial link coupled to a distal end of the pusher assembly and a tether secured to the vaso-occlusive device. In that embodiment, a method of detaching the vaso-occlusive device from the pusher assembly includes applying a first current through the sacrificial link to heat the sacrificial link by resistive heating to a first temperature sufficient to melt the tether without disintegrating the sacrificial link, and applying a second current, greater than the first current, to the sacrificial link to heat the sacrificial link by resistive heating to a second temperature higher than the first temperature, thereby thermally disintegrating the sacrificial link.

In yet another embodiment of the disclosed inventions a vaso-occlusive device delivery assembly includes a pusher assembly having proximal and distal ends, and first and second conductors extending between the proximal and distal ends of the pusher assembly. The vaso-occlusive device delivery assembly also includes a sacrificial link disposed at the distal end of the pusher assembly and electrically connected to the first and second conductors, and a vaso-occlusive device secured to the pusher assembly by the sacrificial link. The sacrificial link includes an electrically conductive member and an electrically insulative member. An insulated portion of the electrically conductive member is disposed in the electrically insulative member, leaving an exposed portion of the electrically conductive member. The vaso-occlusive device is secured to the exposed portion, such that, when a current is applied through the sacrificial link through the first and second conductors, the sacrificial link is heated by resistive heating, causing the exposed portion of the electrically conductive member to thermally disintegrate, thereby detaching the vaso-occlusive device from the pusher assembly.

In some embodiments, the vaso-occlusive member includes a stretch-resisting member having a distal end secured to a distal portion of the vaso-occlusive member and a proximal end secured to an adapter disposed in a lumen of the vaso-occlusive member at a proximal end of the vaso-occlusive member, where the adapter is secured to the electrically conductive portion of the sacrificial link. In those embodiments, the adapter may include a flattened body defining an opening at a distal end thereof, and where the stretch-resisting member forms a loop passing through the opening.

In some embodiments, the vaso-occlusive device is secured to a detachment location on the sacrificial link, where the exposed portion of the electrically conductive member has a cross-sectional area that decreases along a length of the exposed portion to a minimum cross-sectional area proximate the detachment location. Alternatively or additionally, the electrically insulative member may define an opening, where the exposed portion of the electrically conductive member spans through the opening, and the vaso-occlusive device may be secured to the electrically conductive member within the opening.

In various embodiments, the electrically insulative member may be over-molded onto or co-molded with the electrically conductive member.

In still another embodiment of the disclosed inventions, a vaso-occlusive device delivery assembly includes a pusher assembly defining a lumen, a vaso-occlusive device defining a vaso-occlusive device lumen, and releasably attached to the pusher assembly by a connector member. The pusher assembly defines proximal and distal ends, with the pusher lumen extending therebetween. The pusher assembly also includes first and second conductors extending between its proximal and distal ends. The connector member includes a proximal tubular member disposed in the pusher lumen and attached to the pusher assembly, a distal tubular member disposed in the vaso-occlusive device lumen and attached to the vaso-occlusive device, and a sacrificial member electrically connected to the first and second conductors. The sacrificial member includes a proximal portion extending through the proximal connector member, a distal portion extending through the distal connector member, and an exposed middle portion disposed between the proximal and distal connector members, such that, when a current is applied through the sacrificial member through the first and second conductors, the sacrificial member is heated by resistive heating, causing the middle portion of the sacrificial member to thermally disintegrate, thereby detaching the vaso-occlusive device from the pusher assembly. The vaso-occlusive device may include a stretch-resisting member having a distal end secured to a distal portion of the vaso-occlusive device, where a distal end connector portion of the sacrificial member extends distally of the distal connector member, and is secured to a proximal end of the stretch-resisting member.

In yet another embodiment of the disclosed inventions, a vaso-occlusive device delivery assembly includes a pusher assembly defining proximal and distal ends, with first and second conductors extending between the proximal and distal ends; and a vaso-occlusive device releasably attached to the pusher assembly by a connector member. The connector member includes a proximal connecting member secured to the pusher assembly, a distal connecting member secured to the vaso-occlusive device, and a sacrificial member electrically connected to the first and second conductors. The sacrificial member includes a proximal portion secured within the proximal connecting member, and a distal portion extending distally of the proximal connecting member and secured to the distal connecting member, to thereby attach the pusher assembly to the vaso-occlusive device, such that, when a current is applied through the sacrificial member through the first and second conductors, the sacrificial member is heated by resistive heating, causing the middle portion of the sacrificial member to thermally disintegrate, thereby detaching the vaso-occlusive device from the pusher assembly.

In some embodiments, the proximal and distal connectors each have a flattened profile. The pusher assembly may also include a distal end coil having open pitch windings, and the proximal connector member may define a plurality of fingers that are interlaced between adjacent open pitched windings of the pusher assembly distal end coil. The vaso-occlusive member may include a vaso-occlusive coil having open pitch windings at a proximal end thereof, and the distal connector member may define a plurality of fingers that are interlaced between adjacent open pitched windings at the proximal end of the vaso-occlusive coil.

In any of the above embodiments, the sacrificial link may include titanium, titanium alloy, magnesium, magnesium alloy, or an electrically conductive polymer. The electrically conductive polymer may be selected from the group consisting of polyacetylene, polypyrrole, polyaniline, poly(p-phenylene vinylene), poly(thiophene), poly(3,4-ethylenedioxythiophene), and poly(p-phenylene sulfide). The electrically conductive polymer may also be a powder-filled or fiber-filled composite polymer.

Other and further aspects and features of embodiments of the disclosed inventions will become apparent from the ensuing detailed description in view of the accompanying figures.

BRIEF DESCRIPTION OF THE DRAWINGS

The drawings illustrate the design and utility of embodiments of the disclosed inventions, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments of the disclosed inventions and are not therefore to be considered limiting of its scope.

DETAILED DESCRIPTION OF THE ILLUSTRATED EMBODIMENTS

Figure 1:
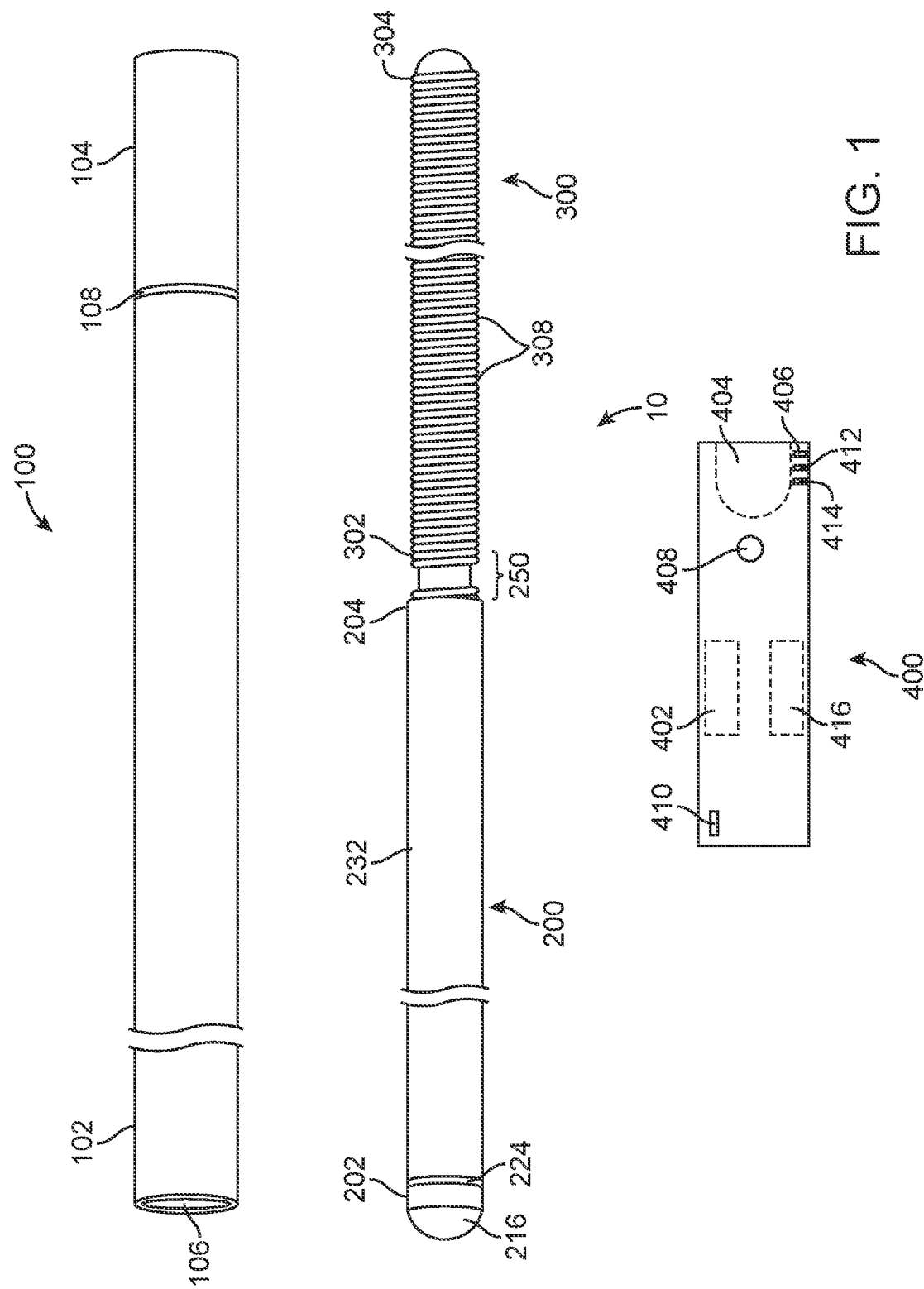
FIG. 1 is a schematic view of a vaso-occlusive device delivery system, according to one embodiment of the disclosed inventions.

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, he terms "about" may include numbers that are rounded to the nearest significant figure.

The recitation of numerical ranges by endpoints includes all numbers within that range (e.g., 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

Various embodiments of the disclosed inventions are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention, which is defined only by the appended claims and their equivalents. In addition, an illustrated embodiment of the disclosed inventions needs not have all the aspects or advantages shown. An aspect or an advantage described in conjunction with a particular embodiment of the disclosed inventions is not necessarily limited to that embodiment and can be practiced in any other embodiments even if not so illustrated.

FIG. 1 illustrates a known vaso-occlusive device delivery system 10. In the system 10 illustrated in FIG. 1, the vaso-occlusive device is a vaso-occlusive coil 300. The system 10 includes a number of subcomponents or subsystems. These include a delivery catheter 100, a pusher assembly 200, a vaso-occlusive coil 300, and a power supply 400. The delivery catheter 100 includes a proximal end 102, a distal end 104, and a lumen 106 extending between the proximal and distal ends 102, 104. The lumen 106 of the delivery catheter 100 is sized to accommodate axial movement of the pusher assembly 200 and the vaso-occlusive coil 300. Further, the lumen 106 is sized for the passage of a guidewire (not shown) which may optionally be used to properly guide the delivery catheter 100 to the appropriate delivery site.

The delivery catheter 100 may include a braided-shaft construction of stainless steel flat wire that is encapsulated or surrounded by a polymer coating. By way of non-limiting example, HYDROLENE® is a polymer coating that may be used to cover the exterior portion of the delivery catheter 100. Of course, the system 10 is not limited to a particular construction or type of delivery catheter 100 and other constructions known to those skilled in the art may be used for the delivery catheter 100. The inner lumen 106 may be advantageously coated with a lubricious coating such as PTFE to reduce frictional forces between the delivery catheter 100 and the respective pusher assembly 200 and vaso-occlusive coil 300 being moved axially within the lumen 106. The delivery catheter 100 may include one or more optional marker bands 108 formed from a radiopaque material that can be used to identify the location of the delivery catheter 100 within the patient's vasculature system using imaging technology (e.g., fluoroscope imaging). The length of the delivery catheter 100 may vary depending on the particular application, but generally is around 150 cm in length. Of course, other lengths of the delivery catheter 100 may be used with the system 10 described herein.

The delivery catheter 100 may include a distal end 104 that is straight as illustrated in FIG. 1. Alternatively, the distal end 104 may be pre-shaped into a specific geometry or orientation. For example, the distal end 104 may be shaped into a "C" shape, an "S" shape, a "J" shape, a 45° bend, a 90° bend. The size of the lumen 106 may vary depending on the size of the respective pusher assembly 200 and vaso-occlusive coil 300, but generally the OD of the lumen 106 of the delivery catheter 100 (I.D. of delivery catheter 100) is less than about 0.02 inches. The delivery catheter 100 is known to those skilled in the art as a microcatheter. While not illustrated in FIG. 1, the delivery catheter 100 may be utilized with a separate guide catheter (not shown) that aids in guiding the delivery catheter 100 to the appropriate location within the patient's vasculature.

Figure 3:
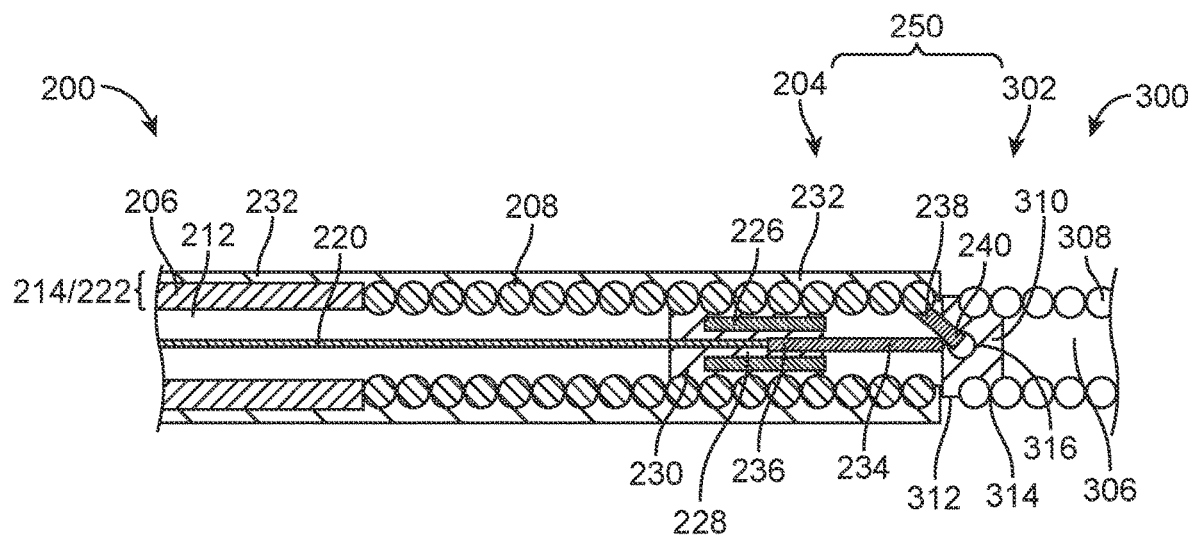
FIGS. 3-18, 24 and 25 are detailed longitudinal cross-sectional views of vaso-occlusive device delivery systems according to various embodiments of the disclosed inventions, which depict the junction between the various pusher assemblies and vaso-occlusive devices.

As illustrated in FIGS. 1 and 3, the system 10 includes a pusher assembly 200 configured for axial movement within the lumen 106 of the delivery catheter 100. The pusher assembly 200 generally includes a proximal end 202 and a distal end 204. The pusher assembly 200 includes a pusher conduit 214, which has a proximal tubular portion 206 and a distal coil portion 208, and defines a pusher lumen 212 and a distal opening in communication with the pusher lumen 212.

FIG. 3 illustrates a detailed longitudinal cross-sectional view of the junction 250 between the pusher assembly 200 and the vaso-occlusive coil 300 according to one embodiment of the disclosed inventions. Similar elements of this embodiment are identified with the same reference numbers as discussed above with respect to FIG. 1. The pusher assembly 200 includes a proximal end 202 and a distal end 204 and measures between around 184 cm to around 186 cm in length. The proximal tubular portion 206 may be formed from, for example, a flexible stainless steel hypotube. The proximal tubular portion 206 may be formed from stainless steel hypotube having an OD of 0.01325 inches and inner diameter (ID) of 0.0075 inches. The length of the hypotube section may be between around 140 cm to around 150 cm, although other lengths may also be used.

A distal coil portion 208 is joined in end-to-end fashion to the distal face of the proximal tubular portion 206. The joining may be accomplished using a weld or other bond. The distal coil portion 208 may have a length of around 39 cm to around 41 cm in length. The distal coil portion 208 may comprise a coil of 0.0025 inches×0.006 inches. The first dimension generally refers to the OD of the coil wire that forms the coil. The latter dimension generally refers to the internal mandrel used to wind the coil wire around to form the plurality of coil winds and is the nominal ID of the coil. One or more windings of the distal coil portion 208 may be formed from a radiopaque material, forming marker coils. For example, the distal coil portion 208 may include a segment of stainless steel coil (e.g., 3 cm in length), followed by a segment of platinum coil (which is radiopaque and also 3 mm in length), followed by a segment of stainless steel coil (e.g., 37 cm in length), and so on and so forth.

An outer sleeve 232 or jacket surrounds a portion of the proximal tubular portion 206 and a portion of the distal coil portion 208 of the pusher conduit 214. The outer sleeve 232 covers the interface or joint formed between the proximal tubular portion 206 and the distal coil portion 208. The outer sleeve 232 may have a length of around 50 cm to around 54 cm. The outer sleeve 232 may be formed from a polyether block amide plastic material (e.g., PEBAX 7233 lamination). The outer sleeve 232 may include a lamination of PEBAX and HYDROLENER that may be heat laminated to the pusher assembly 200. The OD of the outer sleeve 232 may be less than 0.02 inches and advantageously less than 0.015 inches. In the embodiment depicted in FIG. 3, the pusher conduit 214 forms a negative (i.e., return) conductor 222 (described below). Accordingly, the outer sleeve 232 is removed from the very distal end of the pusher conduit 214, during manufacturing, to form an exposed negative electrical contact 224. In other embodiments where the negative conductor 222 is a separate wire running through the pusher conduit 224, the outer sleeve 232 may cover the entire pusher conduit 214, and the negative electrical contact 224 may be a ring electrode disposed around the proximal tubular portion 206 of the pusher conduit 214.

As shown in FIG. 3, the system 10 also includes a proximal seal 230 attached to the interior surface of the distal coil portion 208 of the pusher conduit 214 in the pusher lumen 212. The proximal seal 230 may be formed of an adhesive. A tubular member 226 is disposed in the proximal seal 230 and defines a tube lumen 228. A positive conductor 220 is a wire that runs between the proximal and distal ends 202, 204 of the pusher assembly 200 in the pusher lumen 212 and into the tube lumen 228. The positive conductor 220 extends through the proximal seal 230 while the proximal seal 230 maintains a substantially fluid tight seal between regions proximal and distal of the proximal seal 230.

The positive conductor 220 may be formed from an electrically conductive material, such as copper wire coated with polyimide, with an OD of around 0.00175 inches. The proximal end of the positive conductor 220 is electrically connected to a positive electrical contact 216. As mentioned above, the pusher conduit 214 forms a negative conductor 222, and a portion of the pusher conduit 214 at the proximal end 202 forms a negative electrical contact 224. As shown in FIG. 1, positive and negative electrical contacts 216, 224 are located at the proximal end of the pusher assembly 200. The positive electrical contact 216 may be formed from a metallic solder (e.g., gold). Both the positive and negative electrical contacts 216, 224 may be configured to interface with corresponding electrical contacts (not shown) in the power supply 400 (described below). The positive conductors 220 may be coated with an insulative coating such as polyimide except where it connects to the positive electrical contact 216.

A sacrificial link 234 electrically connects the positive and negative conductors 220, 222, and forms a circuit therewith. The sacrificial link 234 is an elongate body having proximal and distal ends 236, 238. The sacrificial link may be a strand/filament, a tube, or a ribbon. The sacrificial link 234 is partially disposed in the tube lumen 228. The sacrificial link 234 is made from an electrically conductive material such as titanium, titanium alloy, nitinol, magnesium, magnesium alloy, various electrically conductive polymers, and combinations thereof. Electrically conductive polymers include polyacetylene, polypyrrole, polyaniline, poly(p-phenylene vinylene), poly(thiophene), poly(3,4-ethylenedioxythiophene), poly(p-phenylene sulfide), and various powder-filled or fiber-filled composite polymers., such as carbon filled polymers. Powder-filled composite polymers include graphite-filled polyolefins, graphite-filled polyesters, graphite-filled epoxies, graphite-filled silicones, silver-loaded epoxies, and silver-loaded silicones. Fiber-filled composite polymers include carbon fibers, stainless steel fibers, nickel fibers, or aluminum fibers dispersed in polyolefins, polyesters, epoxies, or silicones When a current is applied through the sacrificial link 234, resistance to current flows through the sacrificial link 234 generates heat that thermally disintegrates (i.e., decomposes) the sacrificial link 234, breaking the electrical circuit. Resistance of the sacrificial link 234 is much higher than that of the positive conductor 220 and the conduit 208. The disparity in resistance focuses heat generation focus at the sacrificial link 234. While previously known heat actuated detachment systems utilize separate heating elements to melt attachment members, the system 10 depicted in FIG. 3 uses a conductive and resistive sacrificial link 234 to generate heat to thermally disintegrate itself. The distal coil portion 208 of the pusher assembly does not generate heat that affects the sacrificial link 234, because to current applied through the circuit is relatively low.

The sacrificial link 234 also mechanically connects the vaso-occlusive coil 300 to the pusher assembly 200. The vaso-occlusive coil 300 includes a proximal end 302, a distal end 304, and a lumen 306 extending there between. The vaso-occlusive coil 300 is made from a biocompatible metal such as platinum or a platinum alloy (e.g., platinum-tungsten alloy). The vaso-occlusive coil 300 includes a plurality of coil windings 308. The coil windings 308 are generally helical about a central axis disposed along the lumen 306 of the vaso-occlusive coil 300. The vaso-occlusive coil 300 may have a closed pitch configuration as illustrated in FIGS. 1 and 3. A tether (not shown), such as a suture, may extend from the proximal end 302 through the lumen 306 to the distal end 304 where it is connected to the distal end 304 of the vaso-occlusive coil 300.

Figure 2:
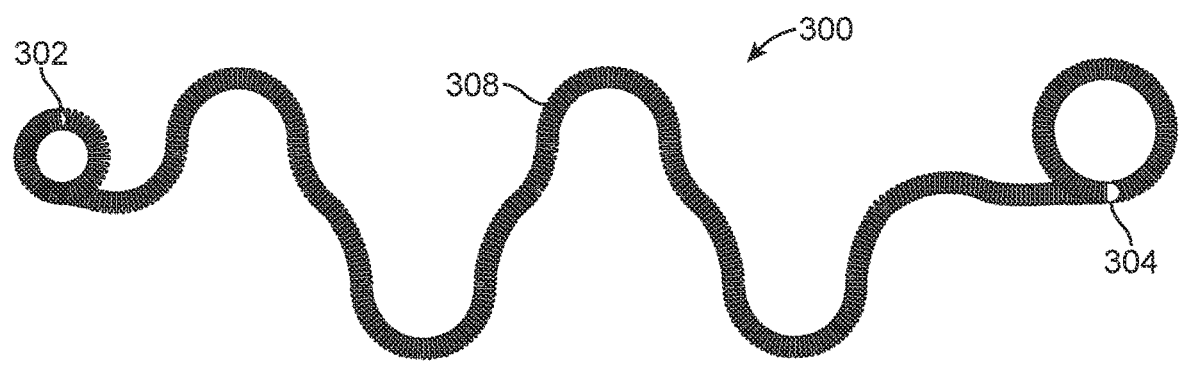
FIG. 2 is a side view of an occlusive coil in a natural state mode, illustrating one exemplary secondary configuration according to an embodiment of the disclosed inventions.

The vaso-occlusive coil 300 generally includes a straight configuration (as illustrated in FIG. 1) when the vaso-occlusive coil 300 is loaded within the delivery catheter 100. Upon release, the vaso-occlusive coil 300 generally takes a secondary shape which may include three-dimensional helical configurations. FIG. 2 illustrates one exemplary configuration of a vaso-occlusive coil 300 in a natural state. In the natural state, the vaso-occlusive coil 300 transforms from the straight configuration illustrated in, for instance, FIG. 1 into a secondary shape. The secondary shaped may include both two and three dimensional shapes of a wide variety. FIG. 2 is just one example of a secondary shape of a vaso-occlusive coil 300 and other shapes and configurations are contemplated to fall within the scope of the disclosed inventions. Also, the vaso-occlusive coil 300 may incorporate synthetic fibers (not shown) over all or a portion of the vaso-occlusive coil 300 as is known in the art. These fibers may be attached directly to coil windings 308 or the fibers may be integrated into the vaso-occlusive coil 300 using a weave or braided configuration. Of course, the system 10 described herein may be used with occlusive coils 300 or other occlusive structures having a variety of configurations, and is not limited to occlusive coils 300 having a certain size or configuration.

The vaso-occlusive coil 300 depicted in FIG. 3 includes an adapter 310 at its proximal end 302. The adapter 310 has proximal and distal portions 312, 314. The adapter 310 may be a flattened body defining an opening 316 at the distal end thereof. The adapter 310 may be formed from a non-conductive material. The distal portion 314 of the adapter 310 is permanently attached to an interior surface of the vaso-occlusive coil 300 at the proximal end of the occlusive coil lumen 306. The distal portion 314 of the adapter 310 may be attached to the occlusive coil with an adhesive.

The proximal portion 312 of the adapter 310 is detachably connected (i.e., releasably attached) to the pusher assembly 200 by the sacrificial link 234. The proximal end 236 of the sacrificial link 234 is mechanically and electrically connected to the positive conductor 220. The sacrificial link 234 also forms a loop 240 passing through the opening 316 in the adapter 310. The distal end 238 of the sacrificial link 234 is mechanically and electrically connected to the negative conductor 222, i.e. the pusher conduit 214. Interference between the loop 240 of the sacrificial link 234 and the opening 316 the adapter 310 mechanically connects the vaso-occlusive device 300 to the pusher assembly 200.

As shown in FIG. 1, the system 10 further includes a power supply 400 for supplying direct current to the positive and negative conductors 220, 222. Activation of the power supply 400 causes electrical current to flow in a circuit including the positive and negative conductors 220, 222 and the sacrificial link 234. The power supply 400 preferably includes an onboard energy source, such as batteries (e.g., a pair of AAA batteries), along with drive circuitry 402. The drive circuitry 402 may include one or more microcontrollers or processors configured to output a driving current. The power supply 400 illustrated in FIG. 1 includes a receptacle 404 configured to receive and mate with the proximal end 202 of the delivery wire assembly 200. Upon insertion of the proximal end 202 into the receptacle 404, the positive, negative electrical contracts 216, 224 disposed on the delivery wire assembly 200 electrically couple with corresponding contacts (not shown) located in the power supply 400.

A visual indicator 406 (e.g., LED light) is used to indicate when the proximal end 202 of delivery wire assembly 200 has been properly inserted into the power supply 400. Another visual indicator 420 is activated if the onboard energy source needs to be recharged or replaced. The power supply 400 includes an activation trigger or button 408 that is depressed by the user to apply the electrical current to the sacrificial link 234 via the positive and negative conductors 220, 222. Once the activation trigger 408 has been activated, the driver circuitry 402 automatically supplies current. The drive circuitry 402 typically operates by applying a substantially constant current, e.g., around 50-1,000 mA. Alternatively, the drive circuitry 402 can operate by applying two different currents, e.g., 350 mA (relatively high current) and 100 mA (relatively low current) for different functions, as described below. A visual indicator 412 may indicate when the power supply 400 is supplying adequate current to the sacrificial link 234.

The power supply 400 may optionally include detection circuitry 416 that is configured to detect when the vaso-occlusive coil 300 has detached from the pusher assembly 200. The detection circuitry 416 may identify detachment based upon a measured impedance value. Another visual indicator 414 may indicate when the occlusive coil 300 has detached from the pusher assembly 200. As an alternative to the visual indicator 414, an audible signal (e.g., beep) or even tactile signal (e.g., vibration or buzzer) may be triggered upon detachment. The detection circuitry 416 may be configured to disable the drive circuitry 402 upon sensing detachment of the occlusive coil 300.

In use, the vaso-occlusive coil 300 is attached to the pusher assembly 200 at junction 250. The attached vaso-occlusive coil 300 and pusher assembly 200 are threaded through the delivery catheter 100 to a target location (e.g., an aneurysm) in the patient's vasculature. Once the distal end 304 of the vaso-occlusive coil 300 reaches the target location, the vaso-occlusive coil 300 is pushed further distally until it's completely exits the distal end 104 of the delivery catheter 100.

In order to detach the vaso-occlusive coil 300 from the pusher assembly 200, the power supply 400 is activated by depressing the trigger 408. The drive circuitry 402 in the power supply 400 applies a current to the positive and negative conductors 220, 222 through the positive and negative electrical contacts 216, 224. As the applied current travels through the sacrificial link 234, the sacrificial link 234 generates heat. The generated heat thermally disintegrates the sacrificial link 234. After activation of the power supply 400, the vaso-occlusive coil 300 is typically detached in less than 1.0 second.

Because most of the sacrificial link 234 is located in the pusher lumen 212, the distal end of the pusher conduit 214 including the distal end of the outer sleeve 232 thermally insulates the sacrificial link 234 from the environment external to the pusher assembly 200. This insulation both protects tissue adjacent the pusher assembly 200 and increases the heat applied to the sacrificial link 234.

The vaso-occlusive device delivery systems 10 depicted in FIGS. 4-7 are similar to the system 10 depicted in FIG. 3. Similar elements of this embodiment are identified with the same reference numbers as discussed above with respect to FIG. 3. A feature common to the systems 10 depicted in FIGS. 4 to 7 that is different from the system 10 depicted in FIG. 3 is that the negative conductor 222 is a wire that runs between the proximal and distal ends 202, 204 of the pusher assembly 200 in the pusher lumen 212, like the positive conductor 220. The positive and negative conductors 220, 222 both run through the proximal seal 230 and the tubular member 226. As described above, in embodiments where both the positive and negative conductors 220, 222 are wires running through the pusher lumen 212, the outer sleeve 232 may cover the entire pusher conduit 214, and the negative electrical contact 224 may be a ring electrode disposed around the proximal tubular portion 206 of the pusher conduit 214 and electrically connected to a proximal end of the negative conductor 222.

Another feature common to the systems 10 depicted in FIGS. 4 to 7 is that the positive and negative conductors 220, 222 are connected to each, other distal of the tubular member, by the sacrificial link 234. In the system 10 depicted in FIG. 4, the sacrificial link 234 is an elongate member 234 connecting the respective distal terminal ends of the positive and negative conductors 220, 222. One of the conductors, in this case the negative conductor 222, forms a loop 240 through the opening 316 in the adapter 310, thereby mechanically connecting the vaso-occlusive coil 300 to the pusher assembly 200. When current is applied through the sacrificial link 234, sacrificial link 234 is thermally disintegrated by resistive heating, thereby releasing the vaso-occlusive coil 300 from the pusher assembly 200.

Figure 4:
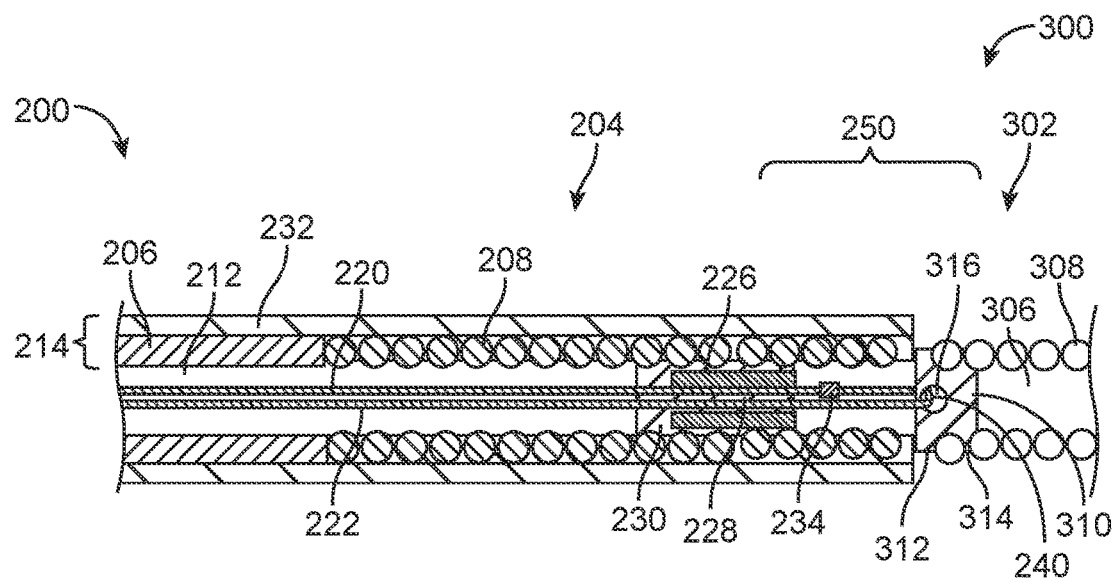
Figure 5:
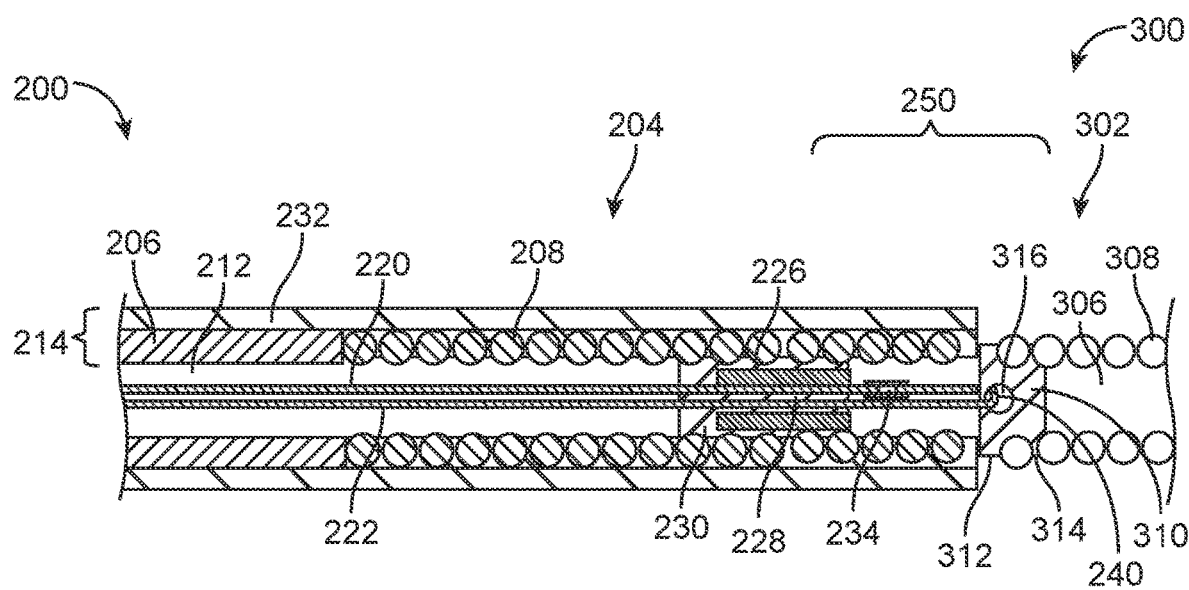

In the system 10 depicted in FIG. 5, the sacrificial link 234 is in the form of a small tube 234. The respective distal ends of the positive and negative conductors 220, 222 extend into the small tube 234 through opposite openings, and are attached to the sacrificial link 234 therein. Otherwise, the system 10 depicted in FIG. 5 is identical to the system 10 depicted in FIG. 4.

Figure 6:
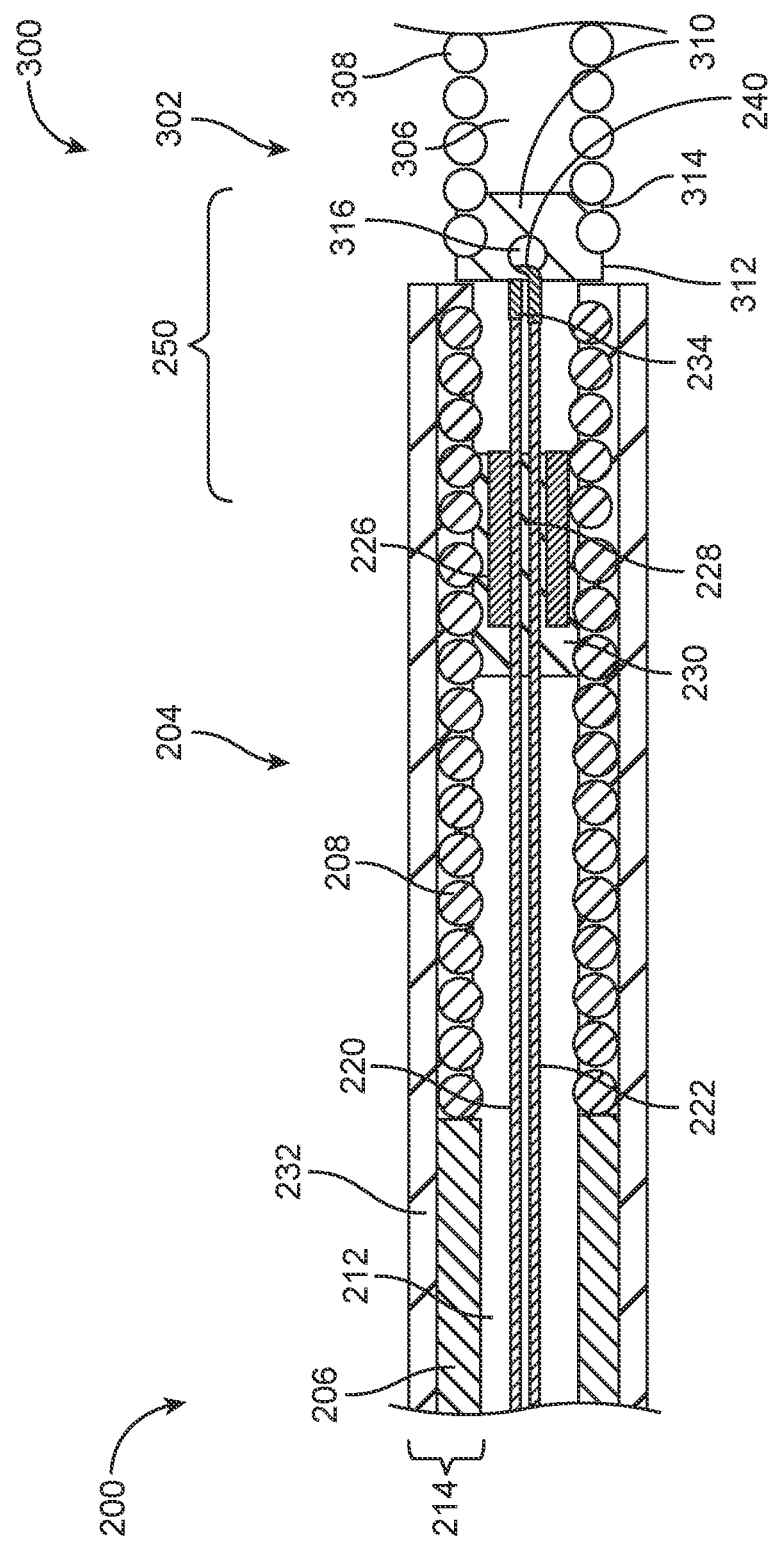

As in the system 10 depicted in FIG. 4, the sacrificial link 234 depicted in FIG. 6 is an elongate member 234 connecting the respective distal terminal ends of the positive and negative conductors 220, 222. In the embodiment depicted in FIG. 6, however, the elongate member 234 forms a loop 240 through the opening 316 in the adapter 310, thereby mechanically connecting the vaso-occlusive coil 300 to the pusher assembly 200. Otherwise, the system 10 depicted in FIG. 6 is identical to the system 10 depicted in FIG. 4.

Figure 7:
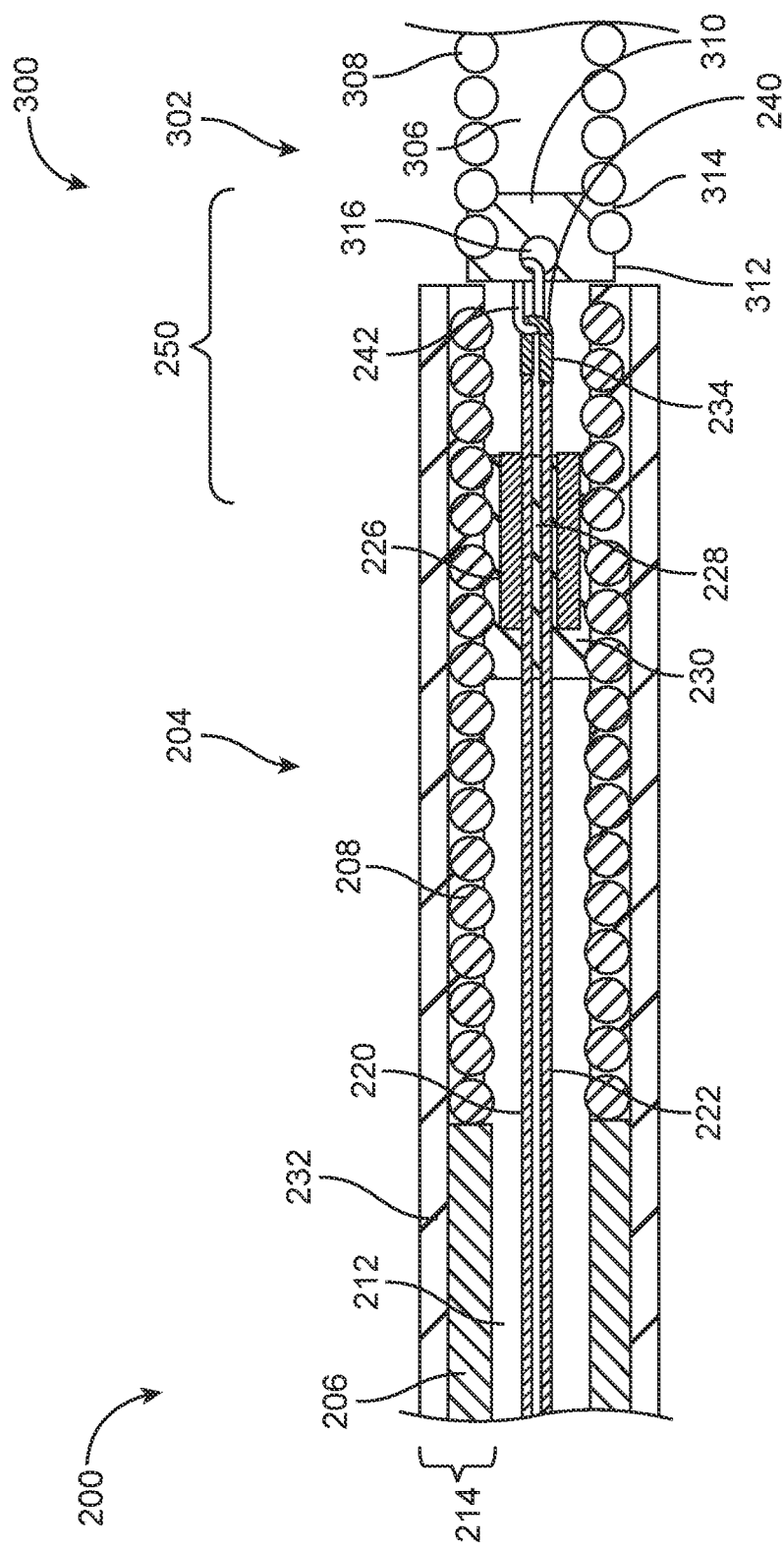

The system 10 depicted in FIG. 7 is similar to the system 10 depicted in FIG. 6. However the loop 240 formed by the elongate member/sacrificial link 234 does not pass through the opening 316 in the adapter 310. Instead a locking ring 242 mechanically connects the elongate member loop 240 to the opening 316 in the adapter 310.

The vaso-occlusive device delivery systems 10 depicted in FIGS. 8-14 are similar to the system 10 depicted in FIG. 3. Similar elements of this embodiment are identified with the same reference numbers as discussed above with respect to FIG. 3. The systems 10 depicted in FIGS. 8, 9, and 11-14 do not have separate insulating tubular members. Instead the sacrificial links 234 are directly connected to the respective pusher conduit 214 in the pusher lumen 212. The arrows in the positive conductor 220, sacrificial link 234, and the pusher conduit 214 illustrate the current flow. The sacrificial links 234 depicted in FIGS. 8 to 14 are cylindrical bodies with an OD approximately equal to the ID of the pusher conduit 214. Therefore, when the sacrificial links 234 are inserted into the respective pusher lumens 212, the outer surface of sacrificial links 234 are in direct contact with an inner surface of the respective pusher conduits 214. The proximal ends 236 of the sacrificial links 234 are also attached to the respective proximal seals 230. The distal ends 238 of sacrificial links 234 are attached to distal seals 318 disposed in the lumens 306 of the respective vaso-occlusive coils 300, thereby connecting the vaso-occlusive coils 300 with the respective pusher assemblies 200. The distal seals 318 can be formed from adhesives.

Figure 8:
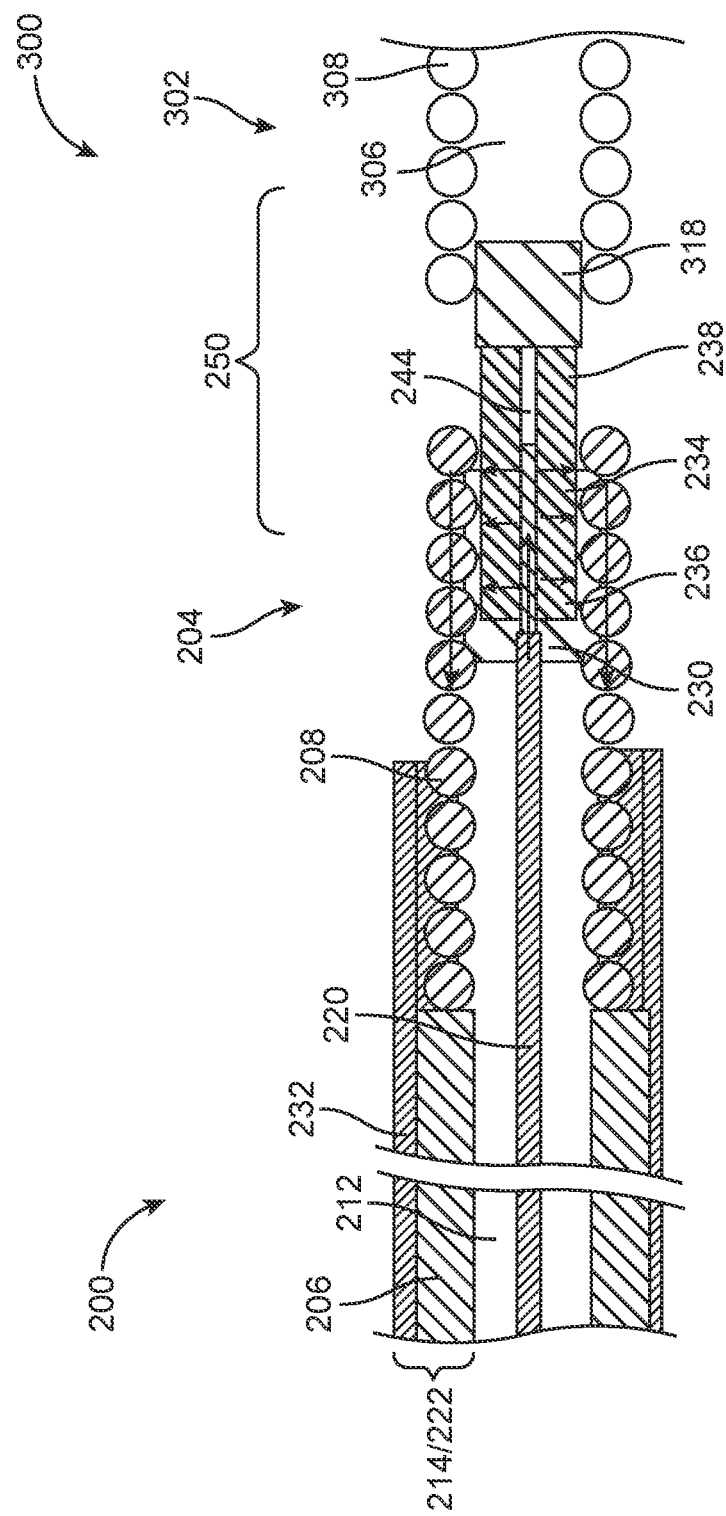

In the system depicted in FIG. 8, sacrificial link 234 is a conductive tube 234 having a conductive tube lumen 244. The distal end of the positive conductor 220 is disposed in the conductive tube lumen 244. The entire portion of the positive connector 220 disposed in the conduct of tube lumen 244 is bare wire in electrical contact with the conductive tube 234. When current is applied through the sacrificial link 234, sacrificial link 234 is thermally disintegrated by resistive heating, thereby releasing the vaso-occlusive coil 300 from the pusher assembly 200. Although the outer sleeve 232 depicted in FIG. 8 does not extend to the distal terminal end of the pusher assembly 200, in other embodiments the outer sleeve 232 can extend to the distal terminal end and distally beyond.

Figure 9:
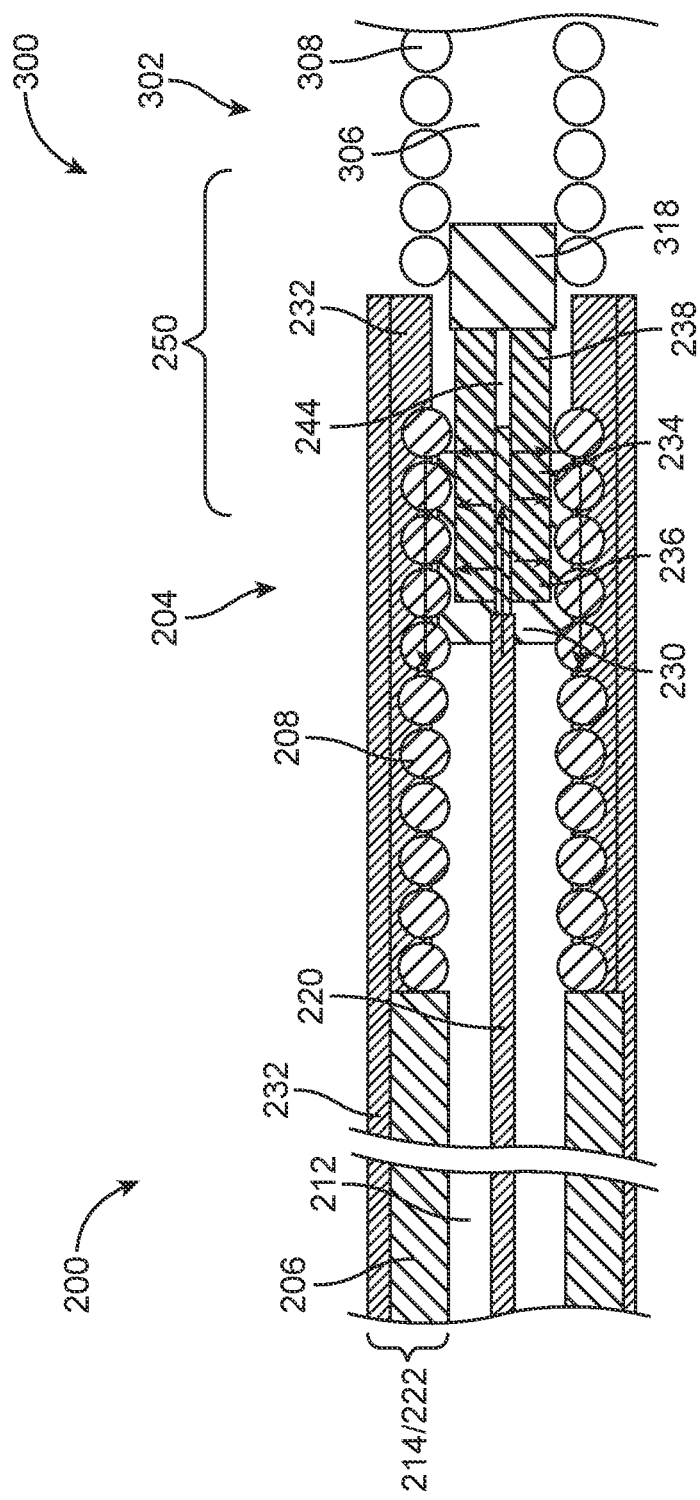

The system 10 depicted in FIG. 9 is similar to the system 10 depicted in FIG. 8, except that the outer sleeve 232 extends further distally in the system 10 depicted in FIG. 9 to cover and further insulate the conductive tube/sacrificial link 234.

Figure 10:
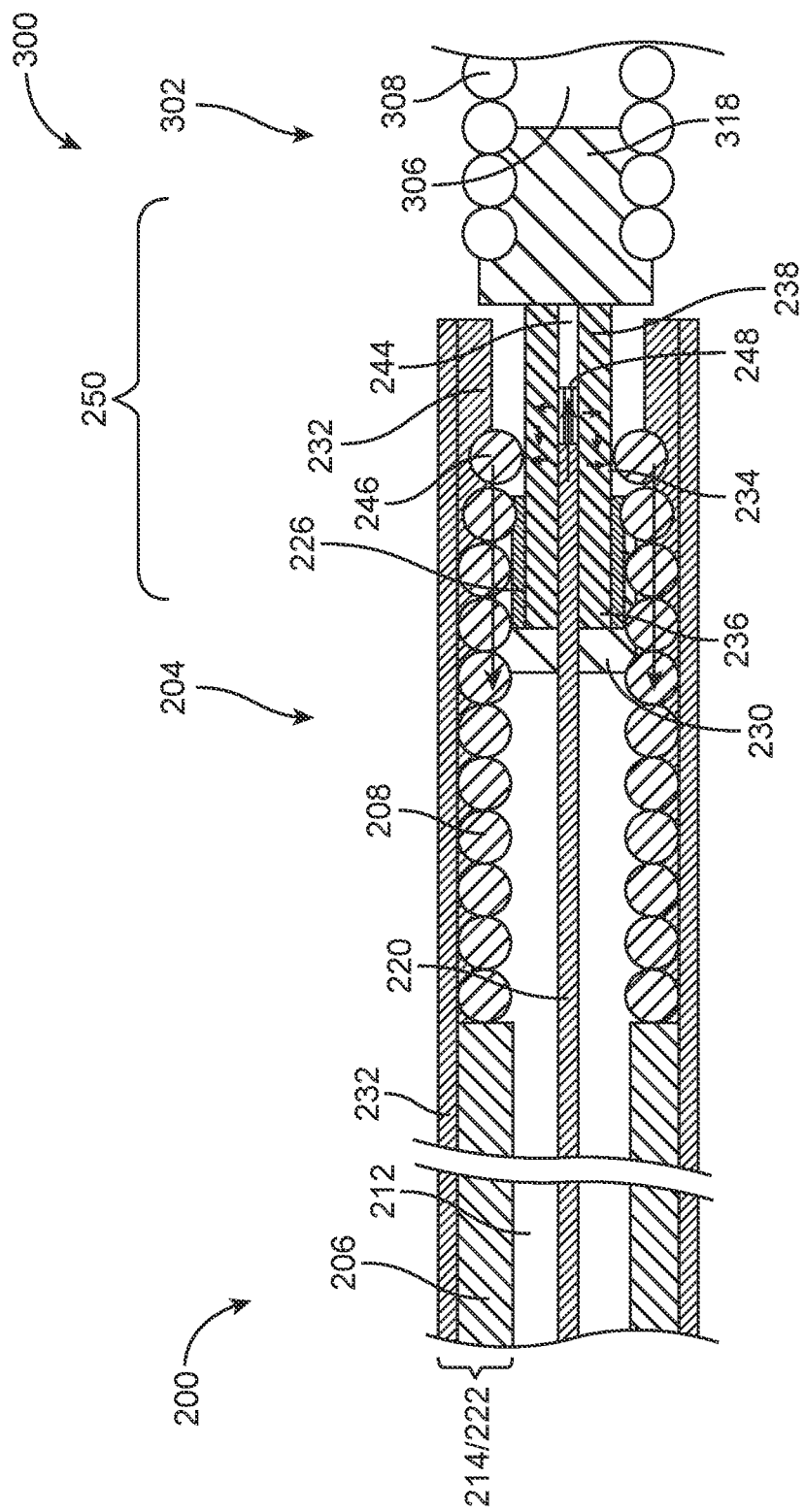

The system 10 depicted in FIG. 10 is similar to the system 10 depicted in FIG. 9, except that an insulating tubular member 226 is disposed around the proximal end 236 of the conductive tube/sacrificial link 234. The tubular member 226 insulates the proximal end 236 of the conductive tube 234 from the negative conductor 222. However the terminal most winding 246 of the negative conductor 222 (pusher conduit 214) extends distally beyond the tubular member 226, thereby electrically connecting the positive and negative conductors 220, 222 through a smaller area. Further, only the distal most portion 248 of the positive conductor 220 is exposed, thereby further reducing the area of electrical contact between the positive and negative conductors 220, 222, and increasing the resistivity of the sacrificial link 234 and the heat generated therein.

The vaso-occlusive device delivery systems 10 depicted in FIGS. 11-14 are similar to the systems 10 depicted in FIG. 8-10. Similar elements of this embodiment are identified with the same reference numbers as discussed above with respect to FIGS. 8-10. The respective sacrificial links 234 depicted in FIGS. 11-14 are elongate bodies 234 defining open proximal ends 236, close distal ends 238, and conductive bore lumens 244. The elongate bodies 234 are connected to respective proximal and distal seals 230, 318, thereby connecting the vaso-occlusive coils 300 from the pusher assemblies 200. The elongate bodies 234 can be injection molded around their respective positive conductors 220.

Figure 11:
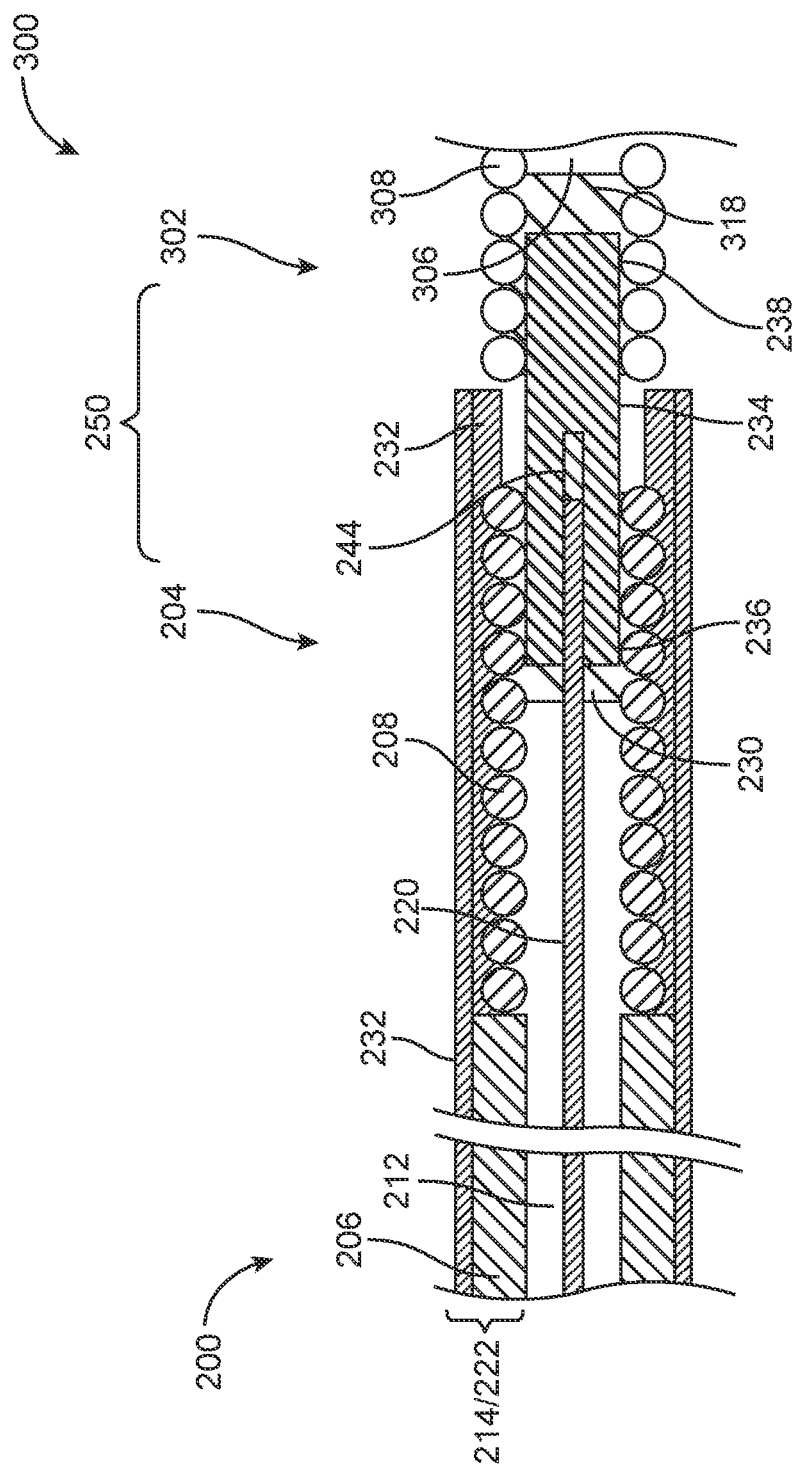
Figure 12:
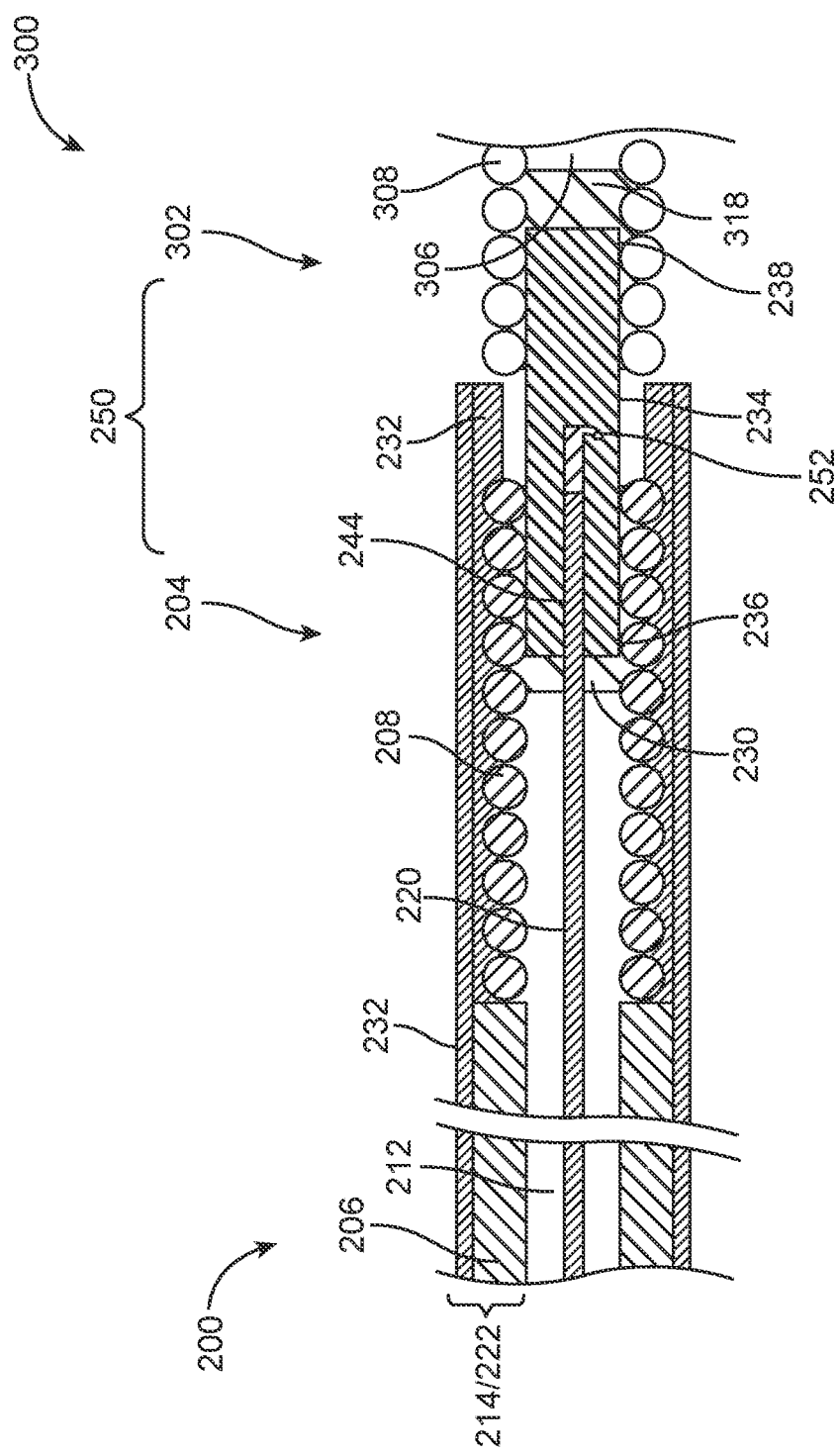

In the system 10 depicted in FIG. 11, the positive conductor 220 extends into the conductive bore lumen 244 and is electrically connected to the elongate body 234 therein. The system 10 depicted in FIG. 12 is similar to the system 10 depicted in FIG. 11, except that the distal end of the positive conductor 220 has a protrusion 252 extending obliquely along a longitudinal axis of the first conductor and into the elongate body 234. The protrusion 252 forms a hook securing the positive conductor 220 in the elongate body 234, and strengthening the mechanical connection therebetween.

Figure 13:
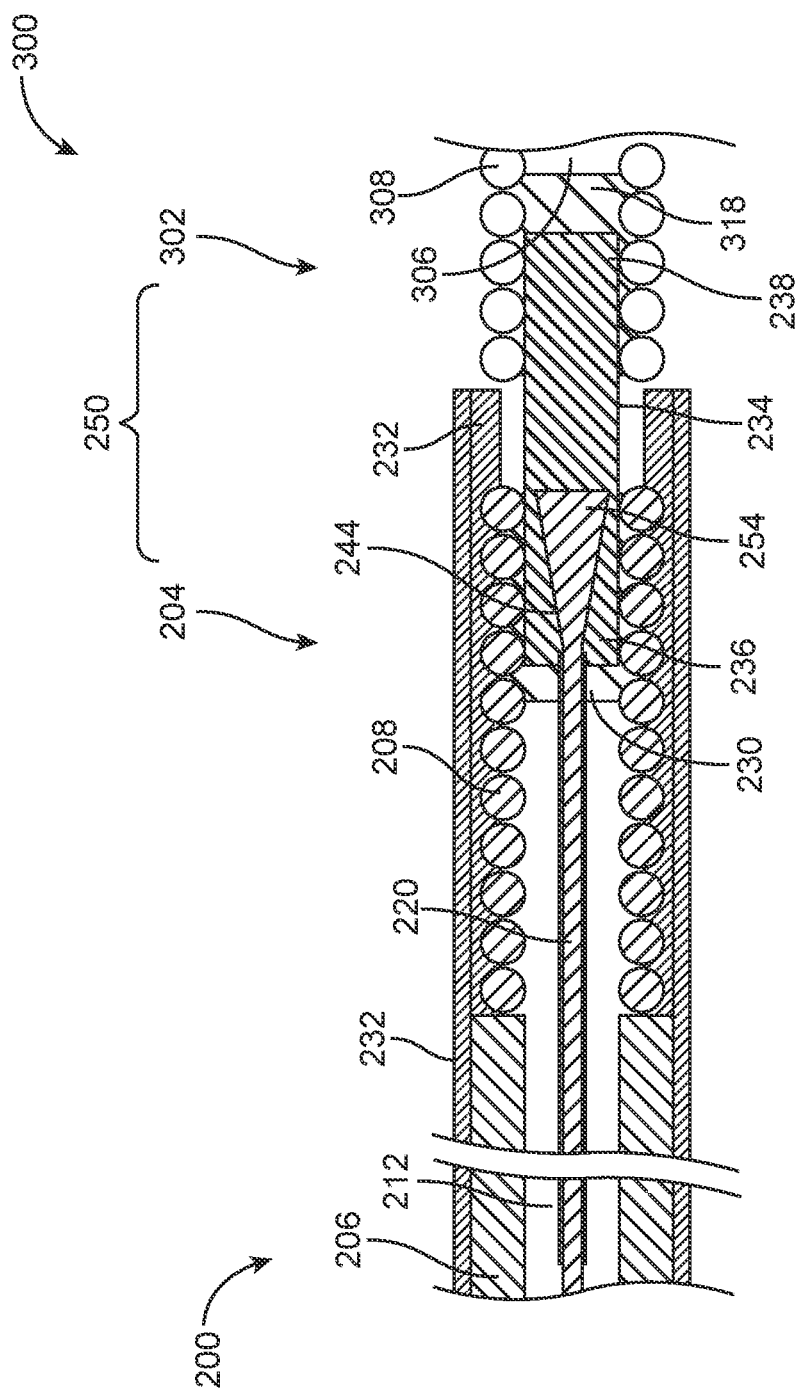

The system 10 depicted in FIG. 13 is similar to the system 10 depicted in FIG. 12. Instead of an oblique protrusion, the distal end of the positive connector 220 includes a radially enlarged portion 254 but also strengthens the mechanical connection between the positive conductor 220 and the conductor bore 234. The radially enlarged portion 254 also concentrates current density in the distal end of the positive connector 220.

Figure 14:
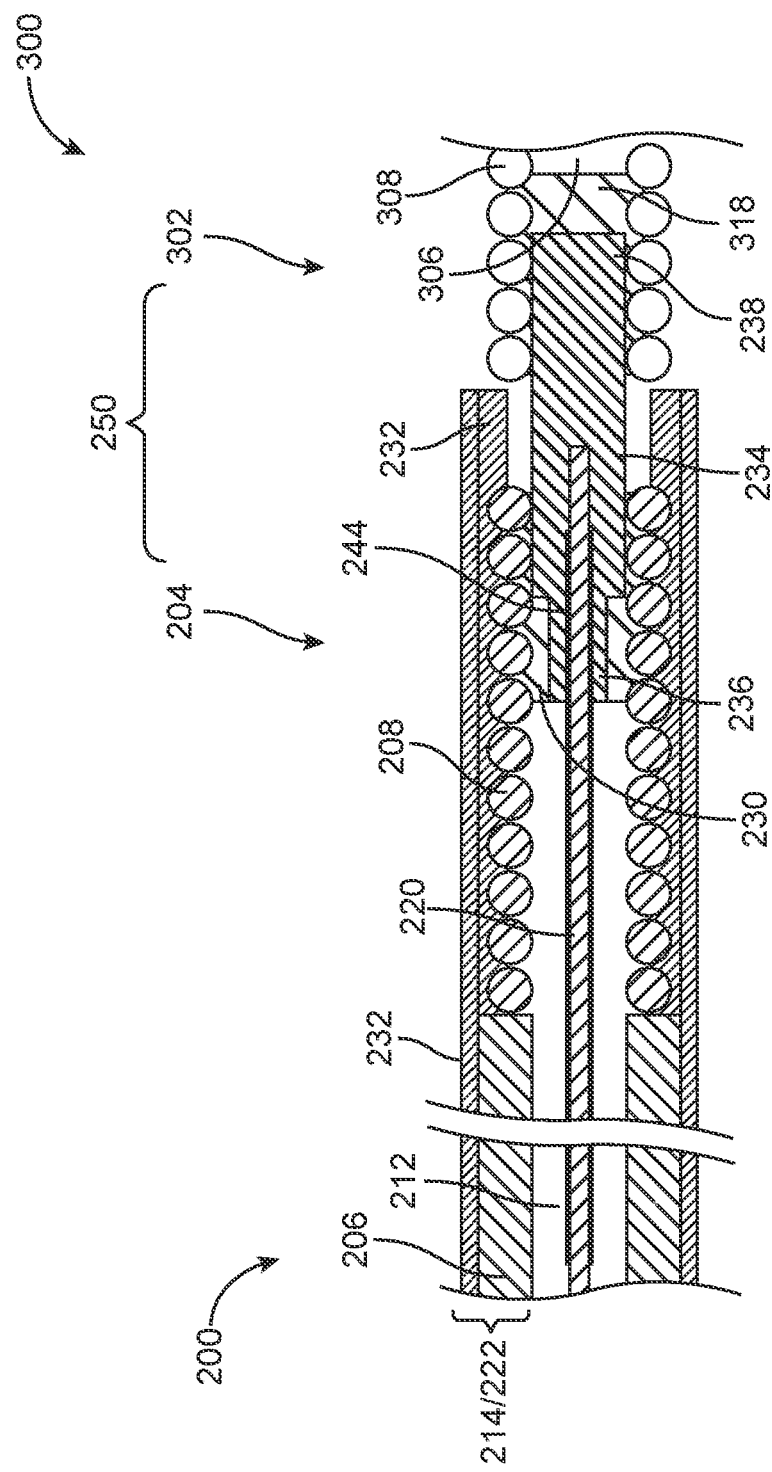

System depicted in FIG. 14 this similar to the system 10 depicted in FIG. 11, except that the proximal end 236 of the elongate body 234 extends completely through the proximal seal 230. This design facilitates separation of vaso-occlusive coil 300 from the pusher assembly 200.

Figure 15:
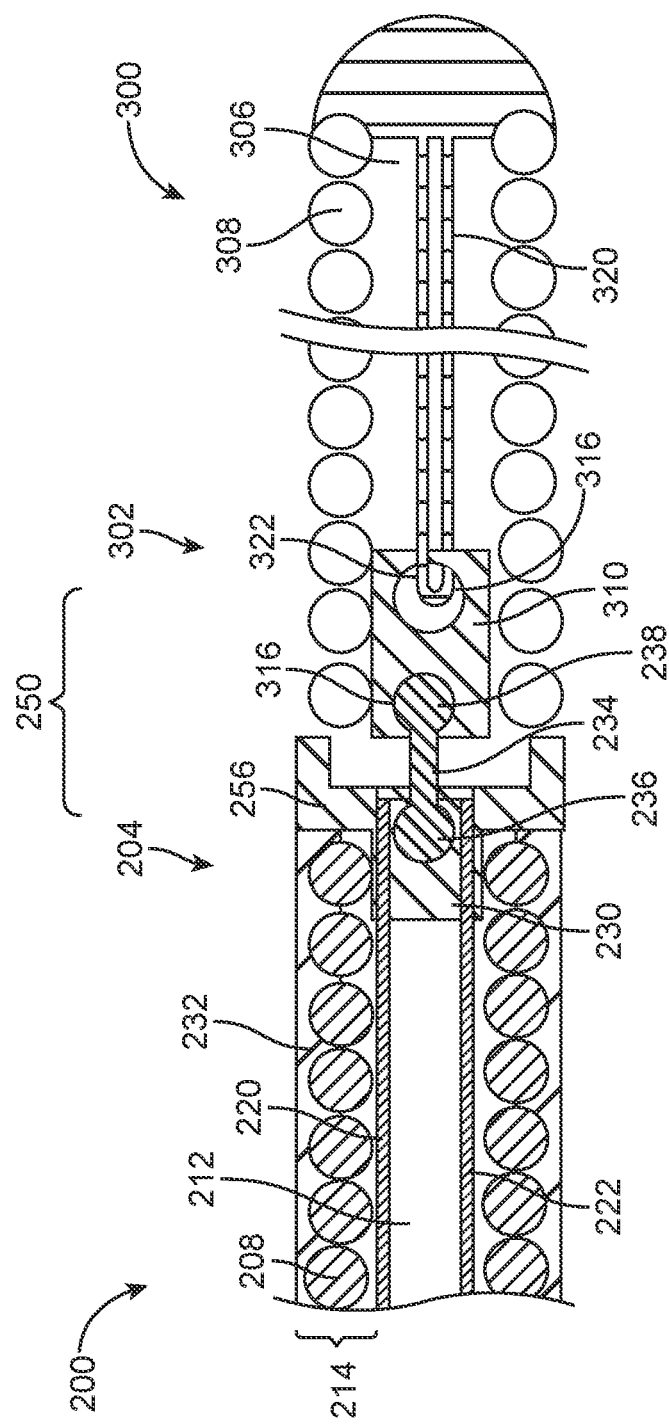

The vaso-occlusive device delivery system 10 depicted in FIG. 15 is similar to the system 10 depicted in FIG. 3. Similar elements of this embodiment are identified with the same reference numbers as discussed above with respect to FIG. 3. The proximal and distal ends 236, 238 of the sacrificial link 234 form proximal and distal spherical enlargements 236, 238, respectively, forming a "dog-bone" shape. The proximal spherical enlargement 236 is disposed in and connected to the proximal seal 230, which is itself connected to the distal end of the pusher conduit 214. The proximal seal 230 may be made from a non-conductive polymer, and includes distally extending portion 256 that thermally insulates the sacrificial link 234.

The distal spherical enlargement 238 is disposed in an opening 316 in the adapter 310 and connected to the adapter 310, which is itself connected to the proximal end 302 of the vaso-occlusive coil 300. The proximal and distal spherical enlargements 236, 238 strengthen the mechanical connections between the sacrificial link 234 and the proximal seal 230 and the adapter 310. Further, the vaso-occlusive coil 300 depicted FIG. 15 also includes a stretch-resisting member 320 attached to the distal end 304 of vaso-occlusive coil 300. The proximal end of the stretch-resisting member 320 forms a loop 322 passing through a second opening 316 in the adapter 310, thereby attaching the stretch-resisting member 320 to the adapter 310.

Figure 16:
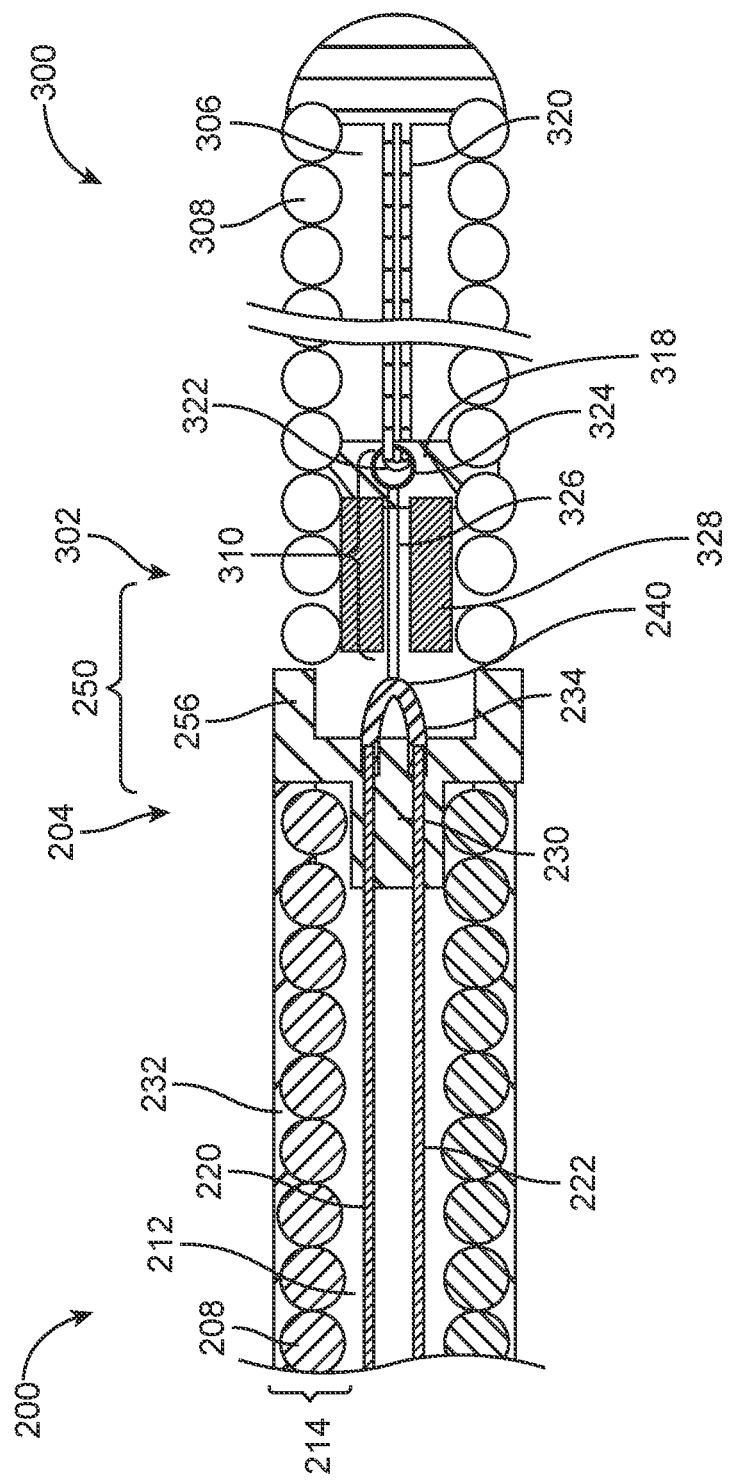

The vaso-occlusive device delivery system 10 depicted in FIG. 16 is similar to the system 10 depicted in FIG. 15. Similar elements of this embodiment are identified with the same reference numbers as discussed above with respect to FIG. 15. The sacrificial link 234 depicted in FIG. 16 is an elongate body forming a loop 240. The sacrificial link 234 is connected to a polymer proximal seal 230 similar to the one depicted in FIG. 15. The adapter 310 includes a ring 324 disposed in the distal seal 318 and the tether 326 extending proximally of the distal seals 318. The tether is threaded through the loop 240 formed by the sacrificial link 234. The stretch-resisting member 320 is threaded through the ring 324 in the adapter 310, thereby connecting the vaso-occlusive coil 300 to the pusher assembly 200. The vaso-occlusive coil 300 also includes a cylindrical member 328 disposed around the tether 326.

Figure 17:
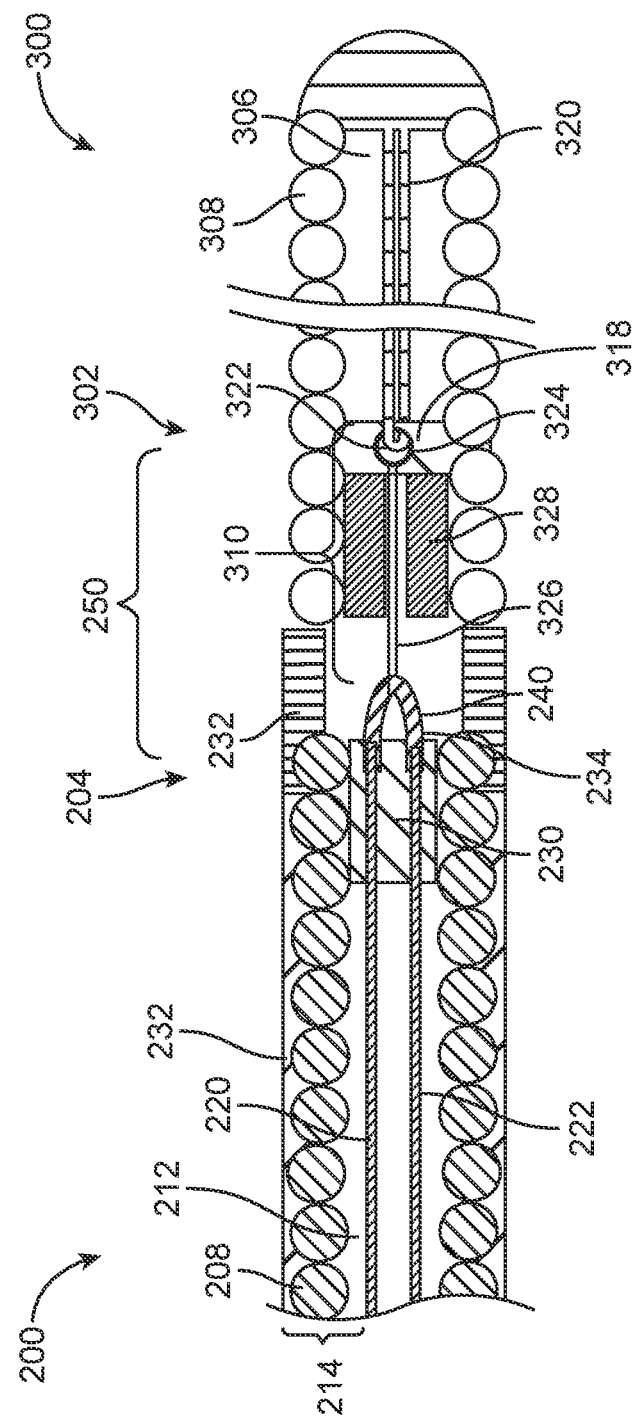

The vaso-occlusive device delivery system 10 depicted in FIG. 17 is similar to the system 10 depicted in FIG. 16. Similar elements of this embodiment are identified with the same reference numbers as discussed above with respect to FIG. 16. There are two differences between the systems 10 depicted in FIGS. 16 and 17. First, the proximal seal 230 depicted in FIG. 17 does not have a distally extending portion like the one depicted in FIG. 16. Instead, the outer sleeve 232 of the pusher assembly 200 extends distally of the pusher conduit 214, thermally insulating the sacrificial link 234.

Figure 18:
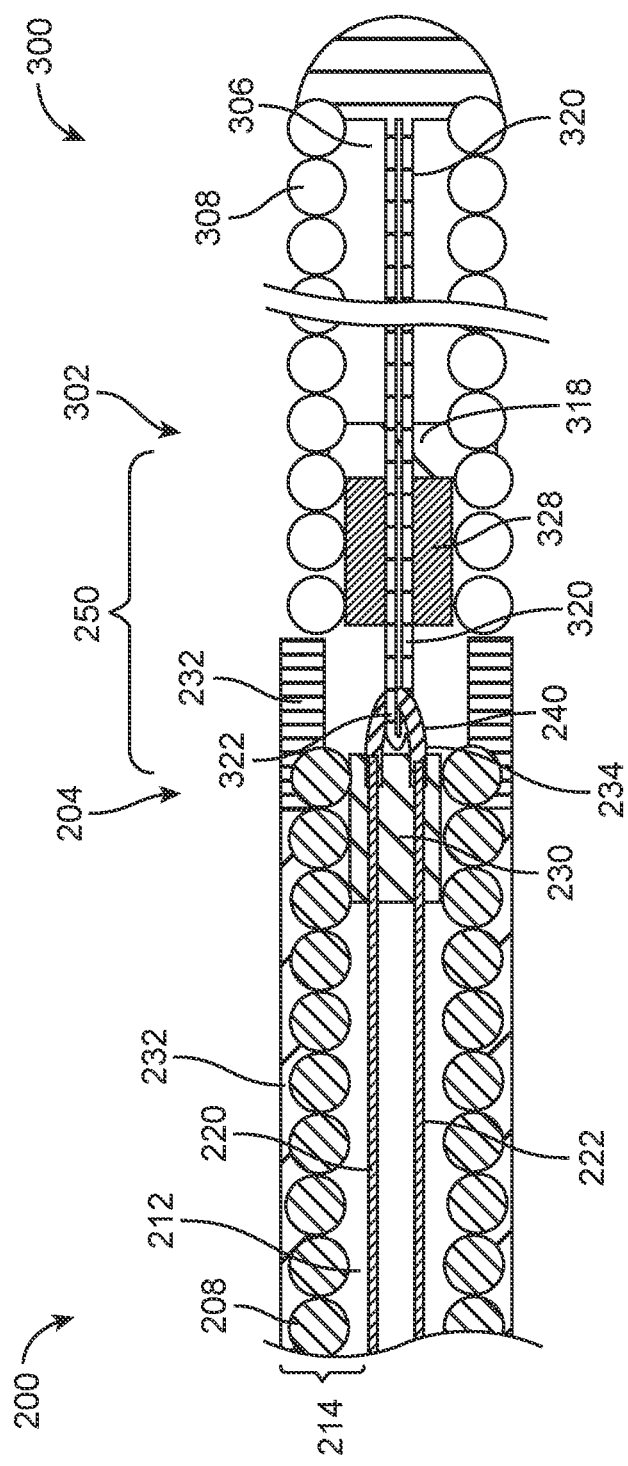
Figure 19:
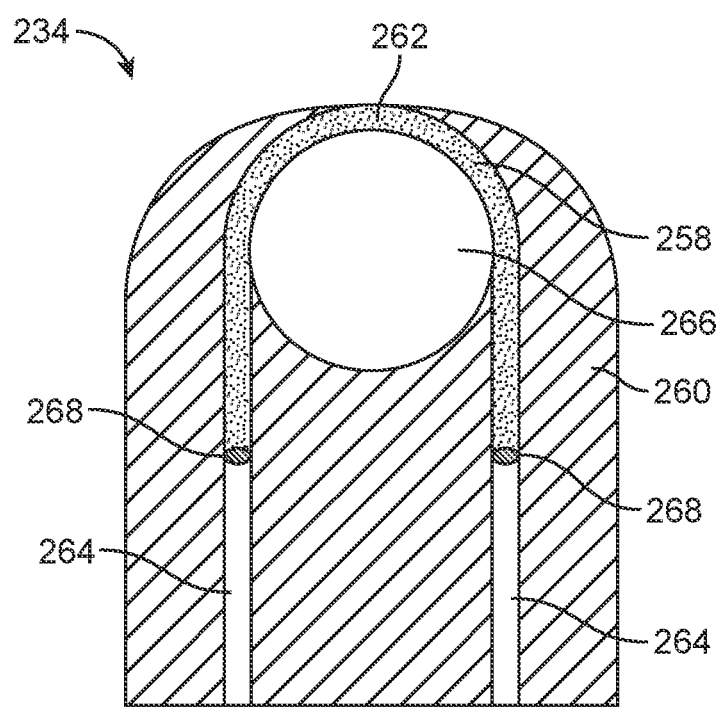
FIGS. 19 and 23 are side views of sacrificial links according to various embodiments of the disclosed inventions.
Figure 20:
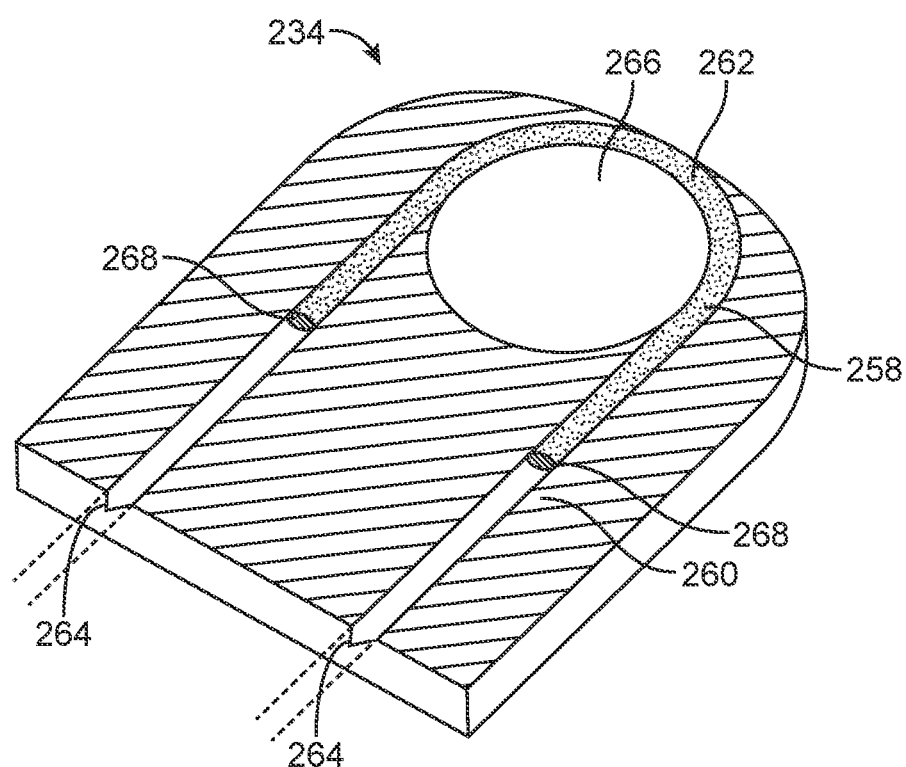
FIGS. 20-22 are perspective views of sacrificial links according to various embodiments of the disclosed inventions.

The vaso-occlusive device delivery system 10 depicted in FIG. 18 is similar to the system 10 depicted in FIG. 17. Similar elements of this embodiment are identified with the same reference numbers as discussed above with respect to FIG. 17. The system 10 depicted in FIG. 18 is not include an adapter like the one depicted in FIG. 17. Instead, the stretch-resisting member 320 extends through the distal seal 318 and the cylindrical member 328 to form a loop 322 through the loop 240 formed by the sacrificial link 234.

Figure 23:
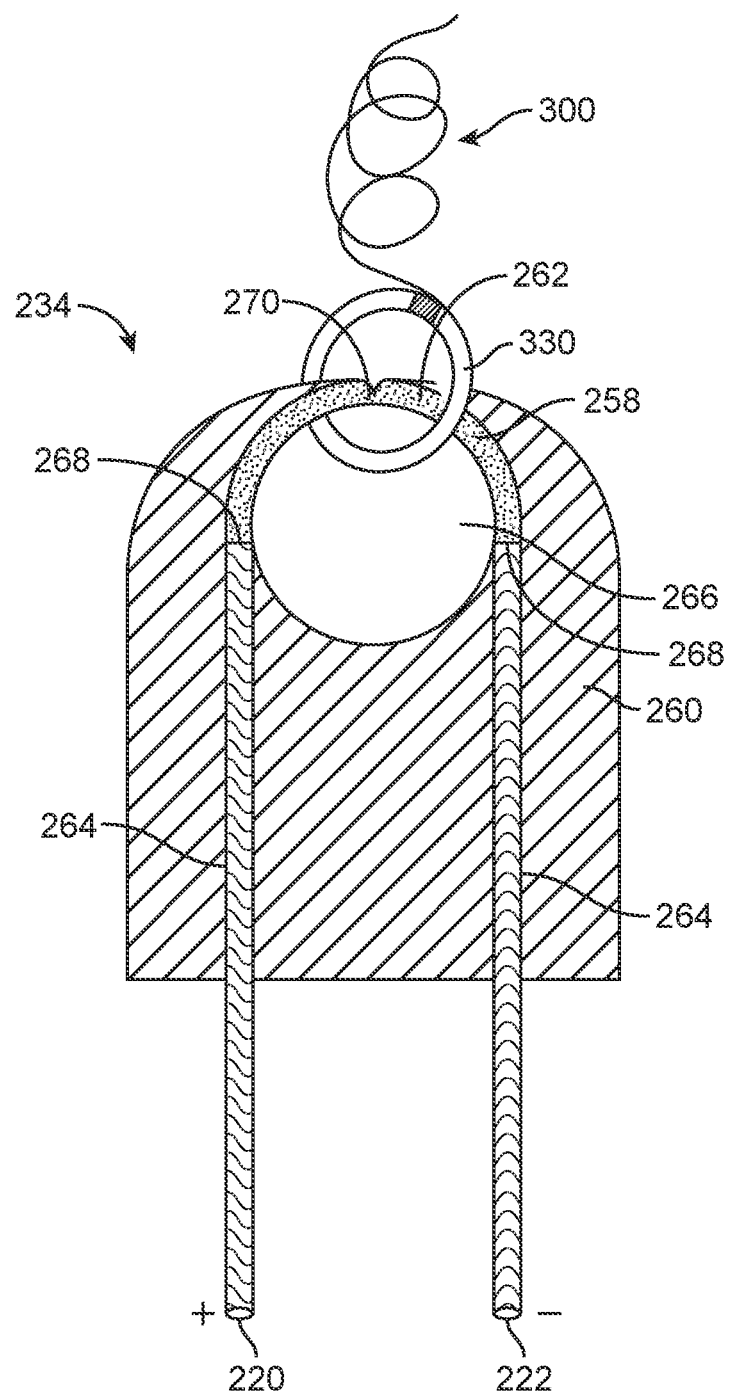

FIGS. 19 to 23 depict a composite sacrificial link 234 for use with any of the above-described embodiments. The sacrificial link 234 includes an electrically conductive member 258 partially disposed in an electrically insulating member 260, leaving an exposed portion 262 of the electrically conductive member 258. Sacrificial link 234 also defines grooves 264 for connecting to positive and negative conductors (see FIG. 23), and an opening 266 for connecting to the vaso-occlusive coil (see FIG. 23). In FIG. 23, the proximal end 302 of the vaso-occlusive coil 300 includes an open winding 330 loop through the opening 266 in the sacrificial link 234. Positive and negative conductors can be electrically connected to the electrically conductive member 258 by a conductive adhesive or welding 268. When a current is applied through the sacrificial link 234, resistive heating thermally disintegrates the exposed portion 262 of the electrically conductive member 258, thereby releasing the vaso-occlusive coil 300 from the pusher assembly 200.

The electrically conductive member 258 can be made of a conductive polymer, such as any those described above. The electrically insulating member can be made from any non-conductive polymer. Rigid non-conductive polymers include polycarbonate and polystyrene. Soft non-conductive polymers include silicone and polyurethane. The sacrificial link 234 can be made by either co-molding the conductive and non-conductive polymers, or over-molding the nonconductive polymer on top of the conductive polymer.

Figure 21:
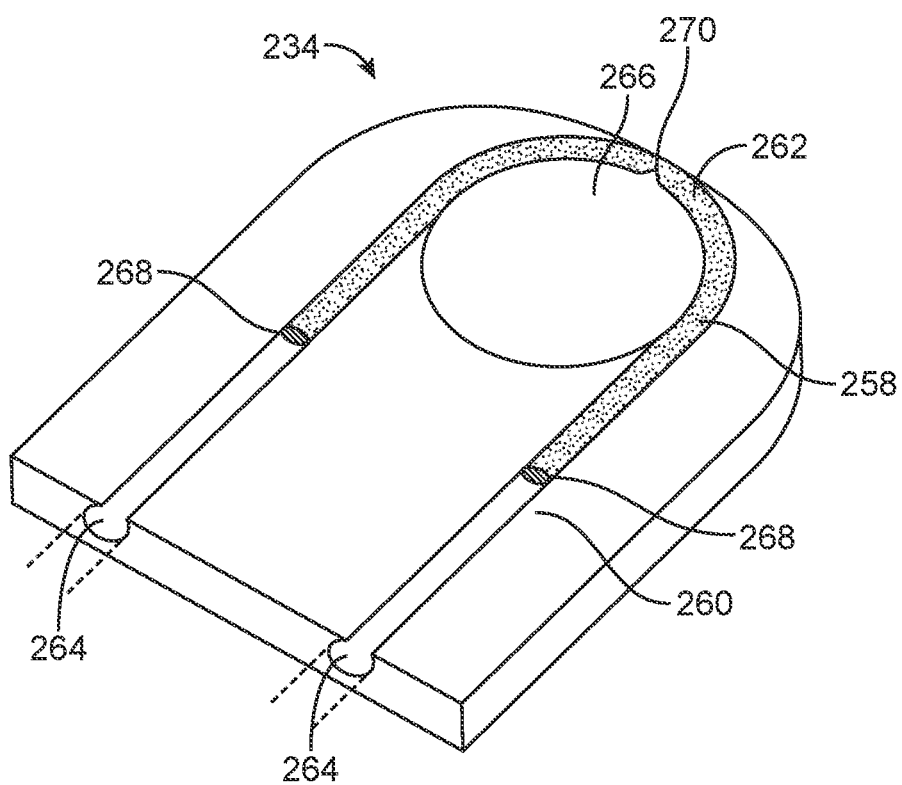
Figure 22:
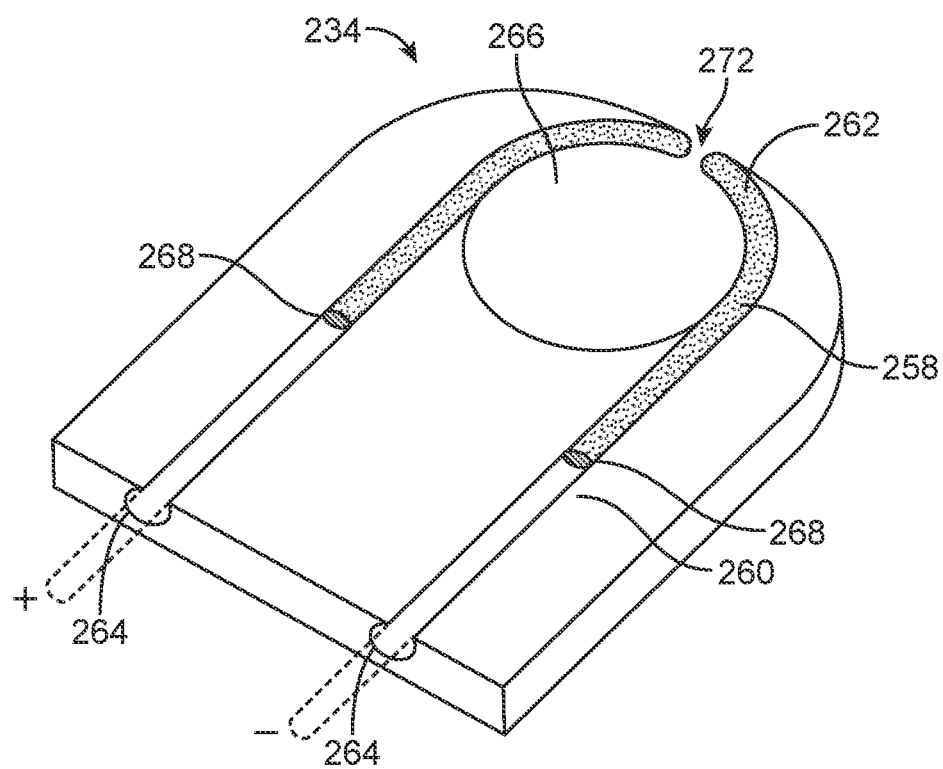

The sacrificial link 234 depicted in FIG. 21 includes a notch 270 in the electrically conductive member 258. As shown in FIG. 21, the cross-sectional area of the electrically conductive member 258 is at a minimum at the notch 270. The decreased cross-sectional area increases resistance, thereby increasing heat generated at the notch 270. The sacrificial link 234 depicted in FIG. 22 includes a small gap 272 in the electrically conductive member 258. When current is applied through the sacrificial link 234, the current will arc through the 272, generating a large amount of heat and sparks to thermally disintegrate the exposed portion 262 of the electrically conductive member 258.

Figure 24:
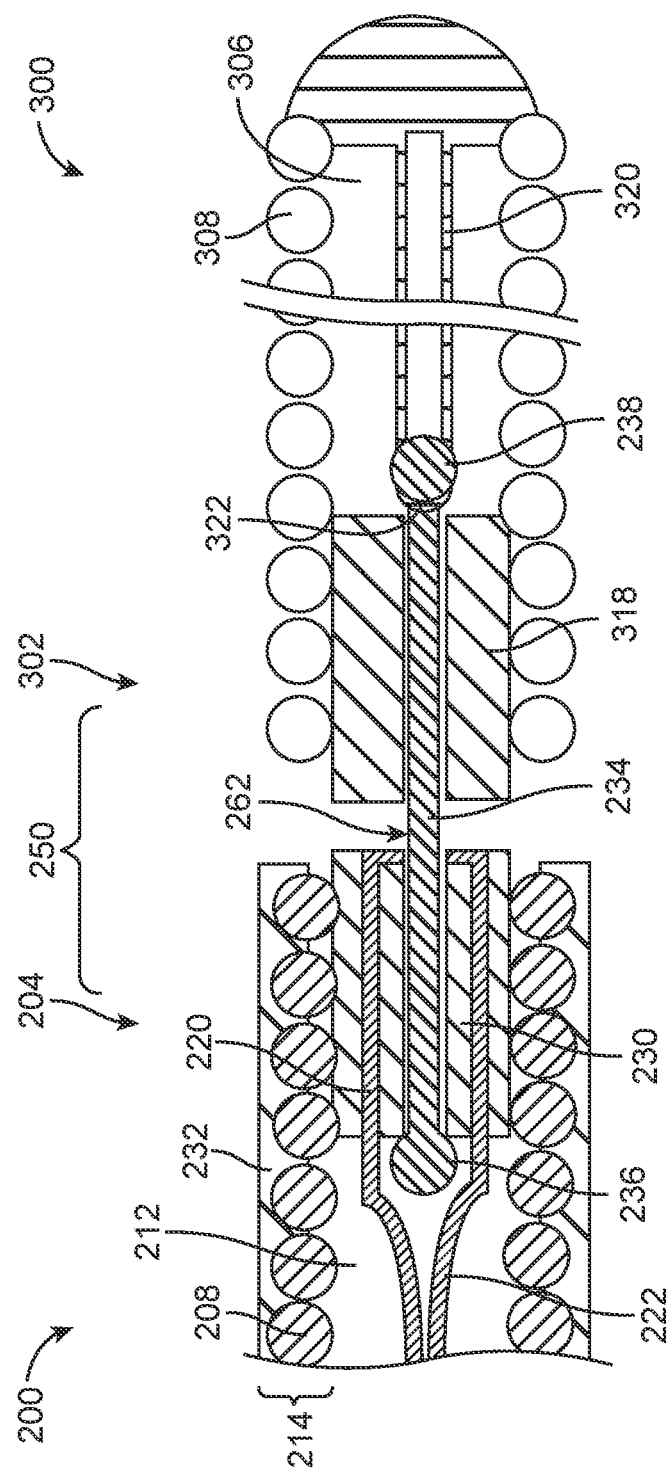

The vaso-occlusive device delivery system 10 depicted in FIG. 24 is similar to the system 10 depicted in FIG. 15. Similar elements of this embodiment are identified with the same reference numbers as discussed above with respect to FIG. 15. Like the sacrificial link 234 depicted in FIG. 15, the sacrificial link 234 depicted in FIG. 24 has proximal and distal spherical enlargements 236, 238 in its proximal and distal ends 236, 238, respectively, forming a "dog-bone" shape. However, the proximal spherical enlargement 236 of the sacrificial link 234 extends proximally of the proximal seal 230, creating a mechanical interference with the proximal seal 230 preventing distal movement of the sacrificial link 234. Further, the distal spherical enlargement 238 to sacrificial link 234 extends distally of the distal seal 318, creating a mechanical interference with the distal seal 318 preventing proximal movement of the sacrificial link 234. Sacrificial link 234 also includes an exposed portion 262 between the proximal and distal seals 230, 318. Moreover, the stretch-resisting member 320 forms a loop 322 around the distal spherical enlargement 238, connecting the stretch-resisting member 320 to the sacrificial link 234. When current is applied through the sacrificial link 234, heat is generated at the exposed portion 262, thermally disintegrating the exposed portion 262 and releasing the vaso-occlusive coil 300 from the pusher assembly 200.

Figure 25:
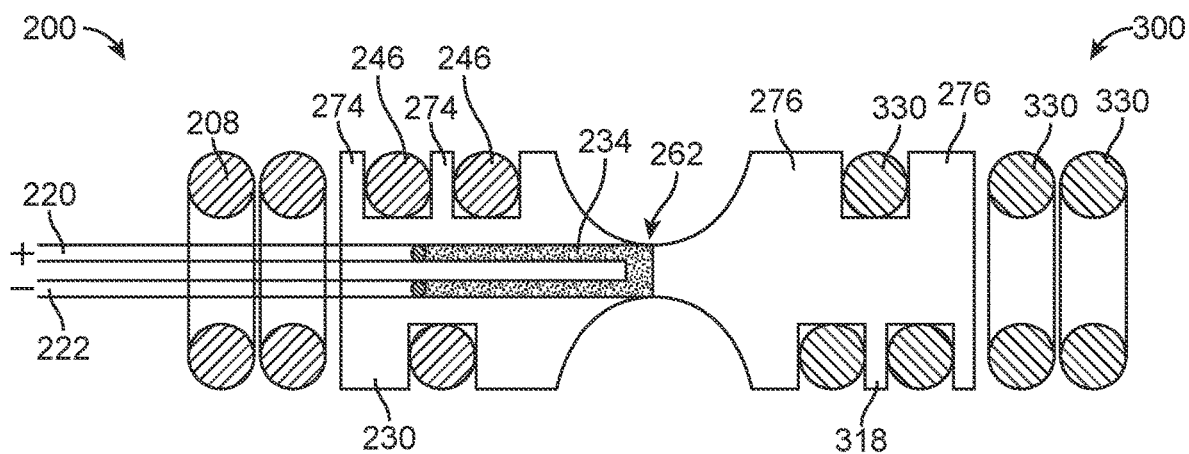

The vaso-occlusive device delivery system 10 depicted in FIG. 25 is similar to the system 10 depicted in FIG. 24. Similar elements of this embodiment are identified with the same reference numbers as discussed above with respect to FIG. 24. The proximal and distal seals 230, 318 depicted in FIG. 25 each have a flat profile. The sacrificial link 234 is disposed in the proximal seal 230, except for an exposed portion 262, which is connected to the proximal end of the distal seal 318. The proximal and distal seals 230, 318 each define respective pluralities of fingers 274, 276. The distal terminal end of the distal coil portion 208 of the pusher conduit 214 and the proximal terminal end of the vaso-occlusive coil 300 each include open windings 246, 330. The fingers 274 defined by the proximal seal 230 are interlaced between adjacent open windings 246 of the distal terminal end of the distal coil portion 208, mechanically connecting the proximal seal 230, and the sacrificial link 234 contained therein, to the pusher conduit 214. The fingers 276 defined by the distal seal 318 are interlaced between adjacent open windings 330 of the proximal terminal end of the vaso-occlusive coil 300, mechanically connecting the distal seal 318, and the sacrificial link 234 attached thereto, to the vaso-occlusive coil 300. When current is applied through the sacrificial link 234, heat is generated at the exposed portion 262, thermally disintegrating the exposed portion 262 and releasing the vaso-occlusive coil 300 from the pusher assembly 200.

Figure 26:
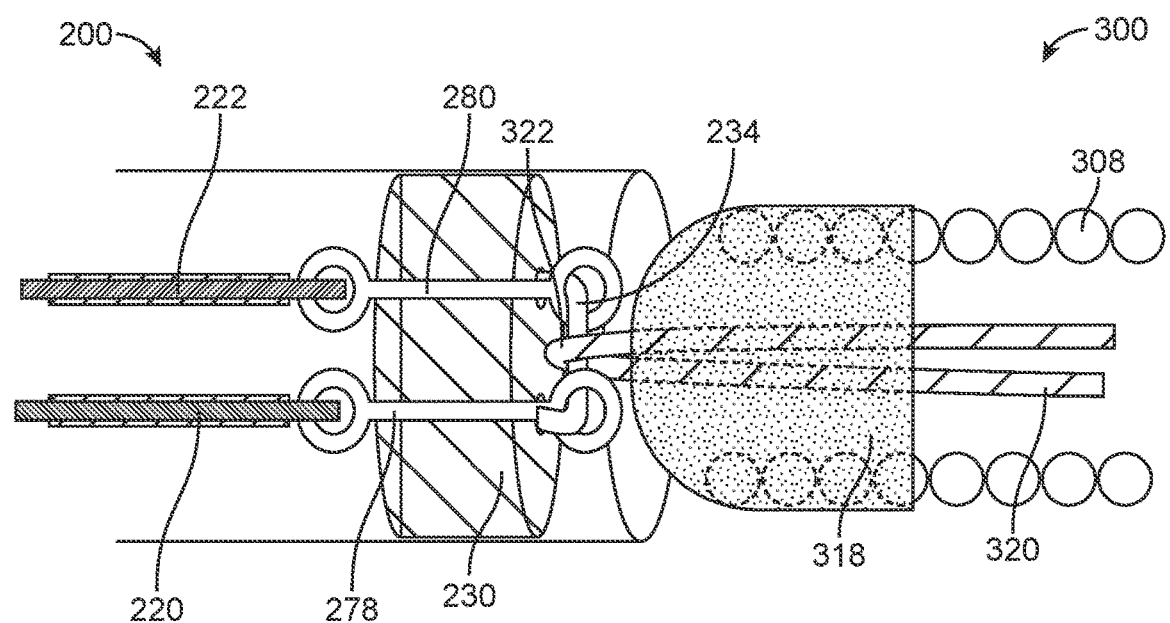
FIGS. 26-28 are detailed schematic views of vaso-occlusive device delivery systems according to various embodiments of the disclosed inventions, which depict the junction between the various pusher assemblies and vaso-occlusive devices.

FIG. 26 illustrates a schematic view of the junction 250 between the pusher assembly 200 and the vaso-occlusive coil 300 according to one embodiment of the disclosed inventions. The system 10 depicted in FIG. 26 is similar to the system 10 depicted in FIG. 18. Similar elements of this embodiment are identified with the same reference numbers as discussed above with respect to FIG. 18. The system 10 includes positive and negative conductors 220, 222 and a sacrificial link 234 connected thereto. The positive and negative conductors 220, 222 are disposed on the proximal side of the proximal seal 230 in the sacrificial link 234 is disposed on the distal side of the proximal seal 230. First and second load bearing connectors 278, 280 connected distal ends of the positive and negative conductors 220, 222 two opposite sides of the sacrificial link 234, respectively. While the first and second load bearing connectors 278, 280 form rings for attachment of the positive and negative conductors 220, 222 and the sacrificial link 234, the load bearing connectors 278, 280 and the positive and negative conductors 220, 222 and the sacrificial link 234 may be tied to each other. Sacrificial link 234 is made of the material such as nitinol (other materials described above) that thermally disintegrates upon application of a relatively high current, for example 350 mA.

A stretch-resisting member 320 passes proximally through the distal seal 318 and forms a loop 322 around the sacrificial link 234, thereby connecting the vaso-occlusive coils 300 to the pusher assembly 200. The stretch-resisting member 320 is formed from a low melting point polymer.

In use the system 10 depicted in FIG. 26 has two modes of operation to detach the vaso-occlusive device 300 from the pusher assembly 200. In the "melting mode," the relatively low current, for example 100 mA, is applied through the sacrificial link 234. This generates small amount of heat, which is not sufficient to generate a temperature that will disintegrate the sacrificial link 234. However, this heat is sufficient to generate a temperature that will melt the stretch-resisting member 320 looping through an in contact with the sacrificial link 234, detaching the vaso-occlusive device 300 the pusher assembly 200. In the "disintegrating mode," a relatively high current, for example 350 mA, is applied through the sacrificial link 234, the relatively high current generates a temperature that thermally disintegrates to sacrificial link 234, detaching the vaso-occlusive device 300 from the pusher assembly 200. The power supply 400 can be controllable to selectively deliver the relatively low current or the relatively high current to the sacrificial link 234.

Figure 27:
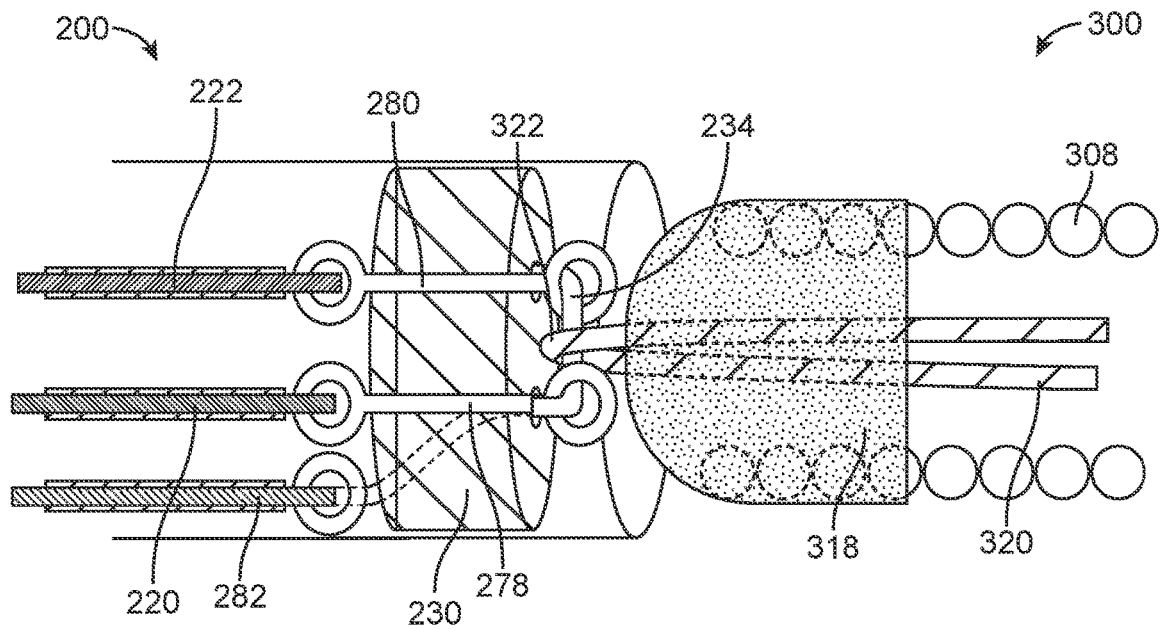

The systems 10 depicted in FIG. 27 is similar to the system 10 depicted in FIG. 26. Similar elements of this embodiment are identified with the same reference numbers as discussed above with respect to FIG. 26. The system depicted in FIG. 27 includes an alternative positive conductor 282, which has a higher resistivity than the positive conductor 220. In this case, the alternative positive conductor 282 has a higher resistivity because it is length of nitinol wire, thereby increasing the total length of nitinol wire in the circuit. The alternative positive conductor 282 is also connected to the sacrificial link 234 such that the alternative positive and negative conductors 282, 222 and the sacrificial link 234 form circuit.

When a relatively high current, is applied through the alternative positive and negative conductors 282, 222 and the sacrificial link 234, the heat generated by the resistance of sacrificial link 234 does not raise the temperature of the sacrificial link 234 sufficiently to thermally disintegrate the sacrificial link 234. However, applying a relatively high current through the alternative positive and negative conductors 282, 222 and the sacrificial link 234 does raise the temperature of sacrificial link 234 sufficiently to melt the stretch-resisting member 320 in contact therewith. Accordingly, the power supply 400 can select between the "melting mode" and "disintegrating mode" by flowing current through either the positive or alternative positive conductors 220, 282, instead of varying the amount of current flowed through the system 10.

Figure 28:
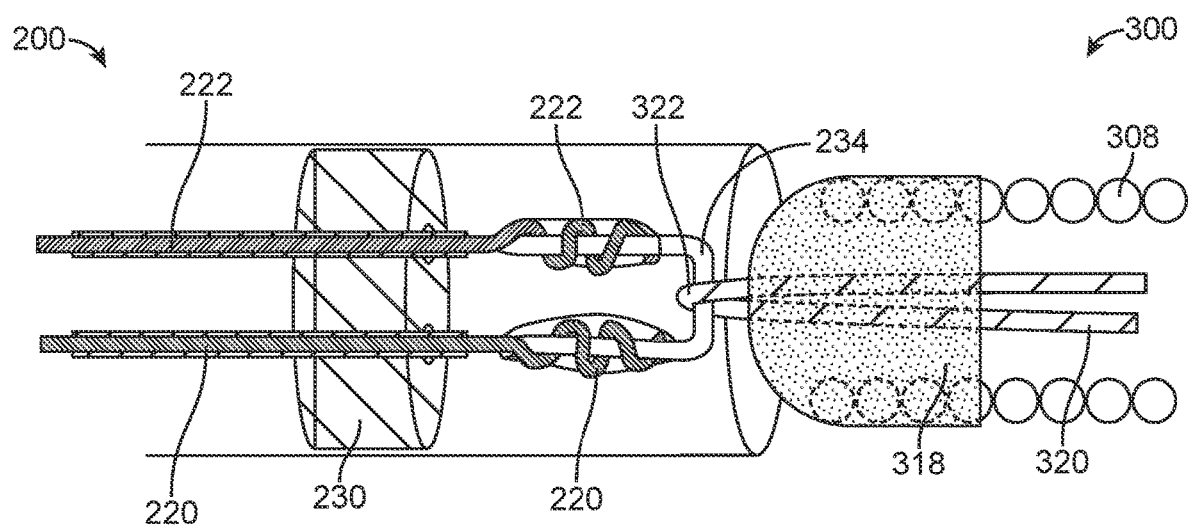

The systems 10 depicted in FIG. 28 is similar to the system 10 depicted in FIG. 26. Similar elements of this embodiment are identified with the same reference numbers as discussed above with respect to FIG. 26. In the system 10 depicted in FIG. 28, the positive and negative conductors 220, 222 extend distally through the proximal seal 230 and connect directly to the sacrificial link 234. In this case, the positive and negative conductors 220, 222 are wrapped around respective opposite ends of the sacrificial link 234 and soldered thereto, mechanically and electrically connecting the conductors 220, 22 to the sacrificial link 234 without load bearing connectors.

Although particular embodiments of the disclosed inventions have been shown and described herein, it will be understood by those skilled in the art that they are not intended to limit the present inventions, and it will be obvious to those skilled in the art that various changes and modifications may be made (e.g., the dimensions of various parts) without departing from the scope of the disclosed inventions, which is to be defined only by the following claims and their equivalents. The specification and drawings are, accordingly, to be regarded in an illustrative rather than restrictive sense. The various embodiments of the disclosed inventions shown and described herein are intended to cover alternatives, modifications, and equivalents of the disclosed inventions, which may be included within the scope of the appended claims.

What is claimed is:

1. A vaso-occlusive device delivery assembly, comprising:
    a pusher assembly, the pusher assembly comprising
        a proximal end,
        a distal end,
        first and second conductors extending between the proximal and distal ends,
        a thermally-degradable conductive sacrificial link disposed at the distal end and electrically coupled between the respective first and second conductors, such that the first conductor, the sacrificial link, and the second conductor form an electrical circuit, and
        an outer sleeve coupled to and completely covering the sacrificial link and configured to thermally insulate the sacrificial link from an environment external to the pusher assembly; and
    a vaso-occlusive device secured to the pusher assembly by the sacrificial link,
    wherein the sacrificial link is configured to generate heat that thermally disintegrates the sacrificial link when a disintegration current is applied through the sacrificial link, thereby releasing the vaso-occlusive device from the pusher assembly, and
    wherein the sacrificial link is a composite sacrificial link that includes an electrically conductive member and an electrically insulating member partially disposed in the electrically conductive member, leaving an exposed portion of the electrically conductive member.

2. The assembly of claim 1, wherein the composite sacrificial link defines an opening to which the vaso-occlusive device is connected.

3. The assembly of claim 1, wherein the electrically conductive member is composed of conductive polymer, and the electrically insulating member is composed of a non-conductive polymer.

4. The assembly of claim 1, wherein the electrically conductive member comprises one of a notch and a small gap.

5. A vaso-occlusive device delivery assembly, comprising:
    a pusher assembly, the pusher assembly comprising
        a proximal end,
        a distal end,
        first and second conductors extending between the proximal and distal ends,
        a thermally-degradable composite sacrificial link disposed at the distal end and electrically coupled between the respective first and second conductors, the composite sacrificial link including an electrically conductive member and an electrically insulating member partially disposed in the electrically conductive member, leaving an exposed portion of the electrically conductive member, such that the first conductor, the electrically conductive member, and the second conductor, respectively, form an electrical circuit, and
        an outer sleeve coupled to and completely covering the sacrificial link and configured to thermally insulate the sacrificial link from an environment external to the pusher assembly; and
    a vaso-occlusive device secured to the pusher assembly by the sacrificial link,
    wherein the composite sacrificial link is configured to generate heat that thermally disintegrates the sacrificial link when a disintegration current is applied through the sacrificial link, thereby releasing the vaso-occlusive device from the pusher assembly, and
    wherein the pusher assembly further comprises a pusher conduit having a lumen, a proximal seal affixed within the lumen of the pusher conduit.

6. The assembly of claim 5, wherein the pusher assembly further comprises a distal seal affixed within a lumen of the vaso-occlusive device.

7. The assembly of claim 5, wherein the sacrificial link comprises a loop connected to the proximal seal.

8. The assembly of claim 5, wherein the composite sacrificial link defines an opening to which the vaso-occlusive device is connected.

9. The assembly of claim 5, wherein the electrically conductive member is composed of conductive polymer, and the electrically insulating member is composed of a non-conductive polymer.

10. The assembly of claim 5, wherein the electrically conductive member comprises one of a notch and a small gap.

11. A vaso-occlusive device delivery assembly, comprising:
    a pusher assembly, the pusher assembly comprising
        a proximal end,
        a distal end,
        first and second conductors extending between the proximal and distal ends,
        a thermally-degradable composite sacrificial link disposed at the distal end and electrically coupled between the respective first and second conductors, the composite sacrificial link including an electrically conductive member and an electrically insulating member partially disposed in the electrically conductive member, leaving an exposed portion of the electrically conductive member, such that the first conductor, the electrically conductive member, and the second conductor, respectively, form an electrical circuit, and an outer sleeve coupled to and completely covering the sacrificial link and configured to thermally insulate the sacrificial link from an environment external to the pusher assembly; and a vaso-occlusive device secured to the pusher assembly by the sacrificial link, wherein the composite sacrificial link is configured to generate heat that thermally disintegrates the sacrificial link when a disintegration current is applied through the sacrificial link, thereby releasing the vaso-occlusive device from the pusher assembly, wherein the pusher assembly further comprises a pusher conduit having a lumen, a proximal seal affixed within the lumen of the pusher conduit, and a distal seal affixed within a lumen of the vaso-occlusive device, and wherein the sacrificial link comprises a loop connected to the proximal seal.

12. The assembly of claim 11, wherein the electrically conductive member is composed of conductive polymer, and the electrically insulating member is composed of a non-conductive polymer.

13. The assembly of claim 12, wherein the electrically conductive member comprises one of a notch and a small gap.

\* \* \* \* \*